(12) United States Patent
Rigo

(10) Patent No.: US 10,407,678 B2
(45) Date of Patent: Sep. 10, 2019

(54) COMPOSITIONS FOR MODULATING EXPRESSION OF C9ORF72 ANTISENSE TRANSCRIPT

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/565,838

(22) PCT Filed: Apr. 16, 2015

(86) PCT No.: PCT/US2015/026218
§ 371 (c)(1),
(2) Date: Oct. 11, 2017

(87) PCT Pub. No.: WO2016/167780
PCT Pub. Date: Oct. 20, 2016

(65) Prior Publication Data
US 2018/0119142 A1  May 3, 2018

(51) Int. Cl.
| | | |
|---|---|---|
| *C12N 15/113* | (2010.01) | |
| *C07H 21/04* | (2006.01) | |
| *A61P 25/28* | (2006.01) | |
| *A61P 25/16* | (2006.01) | |
| *A61P 21/00* | (2006.01) | |
| *C12N 15/11* | (2006.01) | |

(52) U.S. Cl.
CPC ............ *C12N 15/113* (2013.01); *A61P 21/00* (2018.01); *A61P 25/16* (2018.01); *A61P 25/28* (2018.01); *C07H 21/04* (2013.01); *C12N 15/11* (2013.01); *C12N 2310/11* (2013.01); *C12N 2310/315* (2013.01); *C12N 2310/322* (2013.01); *C12N 2310/3231* (2013.01); *C12N 2310/3341* (2013.01); *C12N 2310/341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |

(Continued)

FOREIGN PATENT DOCUMENTS

| | | |
|---|---|---|
| WO | WO 2002/062954 | 8/2002 |
| WO | WO 2005/063976 | 7/2005 |

(Continued)

OTHER PUBLICATIONS

Ash et al., "Unconventional translation of C9ORF72 GGGGCC expansion generates insoluble polypeptides specifict to c9FTD/ASL." Neuron (2013) 77(4):639-646.

(Continued)

*Primary Examiner* — Tracy Vivlemore
(74) *Attorney, Agent, or Firm* — McNeill Baur PLLC

(57) ABSTRACT

Disclosed herein are compositions and methods for modulating expression of C9ORF72 antisense transcript in a cell or animal with C9ORF72 antisense transcript specific inhibitors. Such methods are useful to treat, prevent, or ameliorate neurodegenerative diseases in an individual in need thereof. Such C9ORF72 antisense transcript specific inhibitors include antisense compounds.

35 Claims, No Drawings
Specification includes a Sequence Listing.

(56) References Cited

U.S. PATENT DOCUMENTS

| | | |
|---|---|---|
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,372,492 B1 | 4/2002 | Bennett et al. |
| 6,426,220 B1 | 7/2002 | Bennett et al. |
| 6,525,191 B1 | 2/2003 | Ramasamy |
| 6,531,584 B1 | 3/2003 | Cook et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 | 12/2004 | Hong et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,410,070 B2 | 4/2013 | Miller et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2003/0082807 A1 | 5/2003 | Wengel |
| 2003/0158403 A1 | 8/2003 | Manoharan et al. |
| 2003/0175906 A1 | 9/2003 | Manoharan et al. |
| 2003/0207841 A1 | 11/2003 | Kaneko et al. |
| 2003/0224377 A1 | 12/2003 | Wengel et al. |
| 2004/0143114 A1 | 7/2004 | Imanishi et al. |
| 2004/0171570 A1 | 9/2004 | Allerson et al. |

(56) References Cited

U.S. PATENT DOCUMENTS

| | | | |
|---|---|---|---|
| 2004/0192918 A1 | 9/2004 | Imanishi et al. | |
| 2004/0265230 A1 | 12/2004 | Martinez et al. | |
| 2005/0130923 A1 | 6/2005 | Bhat et al. | |
| 2006/0148740 A1 | 7/2006 | Platenburg | |
| 2006/0286575 A1 | 12/2006 | Farrell et al. | |
| 2008/0039618 A1 | 2/2008 | Allerson et al. | |
| 2010/0190837 A1 | 7/2010 | Migawa et al. | |
| 2010/0197762 A1 | 8/2010 | Swayze et al. | |
| 2011/0123520 A1 | 5/2011 | Manoharan et al. | |
| 2011/0294870 A1 | 12/2011 | Collard et al. | |
| 2013/0130378 A1 | 5/2013 | Manoharan et al. | |
| 2013/0203836 A1 | 8/2013 | Rajeev et al. | |
| 2014/0107330 A1 | 4/2014 | Freier et al. | |
| 2014/0303238 A1 | 10/2014 | Linsley | |
| 2015/0018540 A1 | 1/2015 | Prakash et al. | |
| 2015/0141320 A1 | 5/2015 | Krieg et al. | |
| 2015/0184153 A1 | 7/2015 | Freier et al. | |
| 2015/0191727 A1 | 7/2015 | Migawa et al. | |
| 2015/0267195 A1 | 9/2015 | Seth et al. | |
| 2015/0267197 A1 | 9/2015 | Bennett et al. | |
| 2015/0275212 A1 | 10/2015 | Albaek et al. | |
| 2016/0025747 A1 | 1/2016 | Ranum et al. | |
| 2016/0108396 A1* | 4/2016 | Jensen | C12N 15/111 514/44 A |
| 2016/0230172 A1 | 8/2016 | Rigo | |
| 2016/0237432 A1 | 8/2016 | Bennett et al. | |
| 2018/0016575 A1 | 1/2018 | Hansen et al. | |
| 2018/0023077 A1 | 1/2018 | Rigo | |
| 2018/0142240 A1 | 5/2018 | Bennett et al. | |

FOREIGN PATENT DOCUMENTS

| | | |
|---|---|---|
| WO | WO 2007/056113 | 5/2007 |
| WO | WO 2012/114111 | 8/2012 |
| WO | WO 2014/062691 | 4/2014 |
| WO | WO 2015/057727 | 4/2015 |
| WO | WO 2015/057738 | 4/2015 |
| WO | WO 2016/112132 | 7/2016 |
| WO | WO 2016/167780 | 10/2016 |

OTHER PUBLICATIONS

Baughn et al, "Sense and Anti-Sense RNA Foci in c9ALS/FTD: More Light in a House of Mirrors" Annals of Neurology (Oct. 14, 2013) 74(17): p. S60.

Blitterswijk et al., "How do C9ORF72 repeat expansions cause amyotrophic lateral sclerosis and frontotemporal dementia: can we learn from other noncoding repeat expansion disorders?" Curr Opin Neurol. (2012) 25(6):689-700.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciura et al., "Loss of function of C9orf72 causes motor deficits in a zebrafish model of Amyotrophic Lateral Sclerosis" Annals of Neurology (2013).

Cleveland, D.W., "Gene silencing therapy for human neurodegenerative disease" Oral Presentation, 10th Brain Research Conference, Chicago, IL, Oct. 15, 2015.

Crooke, ST., et al., "Antisense Drug Technology" Second Edition, CRC Press (2008) Chapters 1-28.

Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Extended European Search Report for Application No. 14854291.3 dated Apr. 24, 2017.

Extended European Search Report for Application No. 14854442.2 dated May 17, 2017.

Gautschi et al., "Activity of a novel bcl-2/bcl-xLbispecific antisense oligonucleotide against tumors of diverse histologic origins" J. Natl. Cancer Inst. (2001) 93:463-471.

Gendron et al., "Antisense transcripts of the expanded C9ORF72 hexanucleotide repeat form nuclear RNA foci and undergo repeat-associated non-ATG translation in c9FTD/ALS." Acta Nuropathol (2013) 126(6):829-844.

Gendron et al., "c9RAN Translation: a potential therapeutic target for the treatment of amyotrophic lateral sclerosis and frontotemporal dementia." Expert Opin. Ther. Targets (2013) 17(9):991-995.

Gendron et al., "Disease Mechanisms of C9ORF72 Repeat Expansions" Cold Spring Harbor Perspect Med (Jan. 27, 2017) soi: 10.1101/schperspec.a024224.

Hirtz et al., "How common are the "common" neurologic disorders?" Neurology (2007) 68:326-337.

International Search Report for application No. PCT/US2014/060512 dated Jan. 21, 2015.

International Search Report for application No. PCT/US2014/060530 dated Jan. 21, 2015.

International Search Report for application No. PCT/US2015/026218 dated Oct. 23, 2015.

International Search Report for application No. PCT/US2016/012381 dated May 17, 2016.

Jiang et al. "Gain of Toxicity from ALS/FTG-Linked Repeat Expansions in C9ORF72 is Alleviated by Antisense Oligonucleotides Targeting GGGCC-Containing RNAs." Neuron (2016) 90:535-550.

Jiang et al., "Bidirectional Transcriptinal Inhibition as Therapy for ALS/FTD Caused by Repeat Expanson in C9orf72" Neuron (2016) 92:1160-1163.

Johnson et al., "Exome sequencing reveals VCP mutations as a cause of familial ALS" Neuron (2010) 68:857-864.

Kwiatkowski et al., "Mutations in the FUS/TLS gene on chromosome 16 cause familial amyotrophic lateral sclerosis" Science (2009) 323:1205-1208.

Laaksovirta et al, "Chromosome 9p21 in amyotrophic lateral sclerosis in Finland: a genome-wide association study" Lancet Neurol. (2010) 9:978-985.

Lagier-Tourenne C, et al. "Targeted degradation of sense and antisense C9orf72 RNA foci as therapy for ALS and frontotemporal degeneration" PNAS (2013) 110(47):E4530-E4539.

Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.

Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.

Lillo et al., "Frontotemporal dementia and motor neurone disease: overlapping clinic-pathological disorders" J. Clin. Neurosci. (2009) 16:1131-1135.

Maher et al., "Comparative hybrid arrest by tandem antisense oligodeoxyribonucleotides or oligodeoxyribonucleoside methylphosphonates in a cell-free system" Nucl. Acid. Res. (1998) 16(8):3341-3358.

Maruyama et al., "Mutations of optineurin in amyotrophic lateral sclerosis" Nature (2010) 465:223-226.

Mori et al., "The C9orf72 GGGGCC repeat is translated into aggregating dipeptide-repeat proteins in FTLD/ALS." Science (2013) 339:1335-1338.

Mori et al., Supplemental Material for "The C9orf72 GGGGCC repeat is translated into aggregating dipeptide-repeat proteins in FTLD/ALS." Science (2013) 339:1335-1338.

Morita et al., "A locus on chromosome 9p confers susceptibility to ALS and frontotemporal dementia" Neurology (2006) 66:839-844.

Mulders et al. "Triplet-repeat oligonucleotide-mediated reversal of RNA toxicity in myotonic dysrophy." Proc. Nat. Acad. Sci. USA (2009) 106(33):13915-13920.

(56) References Cited

OTHER PUBLICATIONS

NCBI Reference AC255463 *Homo sapiens* crhromosome 9 clone 174779_ABC12_000049116500_D6. (Jul. 16, 2014) [Retreived from the internet Aug. 17, 2016: <http://www.ncbi.nlm.nih.gov/nuccore/AC255463.1>].

Neumann et al., "Ubiquitinated TDP-43 in frontotemporal lobar degeneration and amyotrophic lateral sclerosis" Science (2006) 314:130-133.

Pearson et al., "Familial frontotemporal dementia with amyotrophic lateral sclerosis and a shared haplotype on chromosome 9p" J. Nerol. (2011) 258:647-655.

Picher-Martel et al., "From Animal Models to Human Disease: A Genetic Approach for Personalized Medicine in ALS" Acta Neuropathologica Communications (2016) 4(70): 1-29.

Renton et al., "A hexanucleotide repeat expansion in C9orf72 is the cause of chromosome 9p21-linked ASL-FTD." Neuron (2011) 72(2):257-268.

Riboldi et al., "Antisense oligonucleotide therapy for the treatment of C9ORF72 ALS/FTD diseases." Mol Nuerobiol (2014) 50(3):721-732.

Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.

Rosen et al., "Mutations in Cu/Zn superoxide dismutase gene are associated with familial amyotrophic lateral sclerosis" Nature (1993) 362:59-62.

Rowland et al., "Amyotrophic lateral sclerosis" N. Engl. J. Med. (2001) 344(22):1688-1700.

Sareen et al., "Targeting RNA foci in iPSC-derived motor neurons from ALS patients with a C9ORF72 repeat expansion." Sci Tran Med (2013) 5(208): 1-13.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Sha et al., "Treatment implications of C9ORF72" Alzheimers Res Ther (2012) 4(6): 46.

Sreedharan et al., "TDP-43 mutations in familial and sporadic amyotrophic lateral sclerosis" Science (2008) 319:1668-1672.

Todd et al, "RNA-Mediated Neurodegeneration in Repeat Expansion Disorders." Annals of Neurology (2010) 67:291-300.

Vance et al., "Familial amyotrophic lateral sclerosis with frontotemporal dementia is linked to a locus on chromosome 9p13.2-21.3" Brain (2006) 129:868-876.

Woolf et al., "Specificity of antisense oligonucleotides in vivo" PNAS (1992) 89: 7305-7309.

Xu et al., "Expanded GGGGCC repeat RNA associated with amyotrophic lateral sclerosis and frontotemporal dementia causes neurodegeneration" Proceedings National Academy of Sciences PNAS (2013) 110(19): 7778-7783.

Zu et al., "RNA proteins and RNA foci from antisense transcripts in C9ORF72 ALS and frontotemoral," PNAS (2013) E4968-E4977.

\* cited by examiner

SEQUENCE LISTING

<160> NUMBER OF SEQ ID NOS: 84

<210> SEQ ID NO 1
<211> LENGTH: 3339
<212> TYPE: DNA
<213> ORGANISM: Homo sapiens
<220> FEATURE:
<221> NAME/KEY: CDS
<222> LOCATION: (203)..(1648)

<400> SEQUENCE: 1

```
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata     180
atgtgacagt tggaatgcag tg atg tcg act ctt tgc cca ccg cca tct cca     232
                         Met Ser Thr Leu Cys Pro Pro Pro Ser Pro
                          1               5                  10 gct gtt gcc aag aca gag att gct tta agt ggc aaa tca cct tta tta     280
Ala Val Ala Lys Thr Glu Ile Ala Leu Ser Gly Lys Ser Pro Leu Leu
             15                  20                  25 gca gct act ttt gct tac tgg gac aat att ctt ggt cct aga gta agg     328
Ala Ala Thr Phe Ala Tyr Trp Asp Asn Ile Leu Gly Pro Arg Val Arg
         30                  35                  40 cac att tgg gct cca aag aca gaa cag gta ctt ctc agt gat gga gaa     376
His Ile Trp Ala Pro Lys Thr Glu Gln Val Leu Leu Ser Asp Gly Glu
     45                  50                  55 ata act ttt ctt gcc aac cac act cta aat gga gaa atc ctt cga aat     424
Ile Thr Phe Leu Ala Asn His Thr Leu Asn Gly Glu Ile Leu Arg Asn
 60                  65                  70 gca gag agt ggt gct ata gat gta aag ttt ttt gtc ttg tct gaa aag     472
Ala Glu Ser Gly Ala Ile Asp Val Lys Phe Phe Val Leu Ser Glu Lys
 75                  80                  85                  90 gga gtg att att gtt tca tta atc ttt gat gga aac tgg aat ggg gat     520
Gly Val Ile Ile Val Ser Leu Ile Phe Asp Gly Asn Trp Asn Gly Asp
                 95                 100                 105 cgc agc aca tat gga cta tca att ata ctt cca cag aca gaa ctt agt     568
Arg Ser Thr Tyr Gly Leu Ser Ile Ile Leu Pro Gln Thr Glu Leu Ser
            110                 115                 120 ttc tac ctc cca ctt cat aga gtg tgt gtt gat aga tta aca cat ata     616
Phe Tyr Leu Pro Leu His Arg Val Cys Val Asp Arg Leu Thr His Ile
        125                 130                 135 atc cgg aaa gga aga ata tgg atg cat aag gaa aga caa gaa aat gtc     664
Ile Arg Lys Gly Arg Ile Trp Met His Lys Glu Arg Gln Glu Asn Val
    140                 145                 150 cag aag att atc tta gaa ggc aca gag aga atg gaa gat cag ggt cag     712
Gln Lys Ile Ile Leu Glu Gly Thr Glu Arg Met Glu Asp Gln Gly Gln
155                 160                 165                 170 agt att att cca atg ctt act gga gaa gtg att cct gta atg gaa ctg     760
Ser Ile Ile Pro Met Leu Thr Gly Glu Val Ile Pro Val Met Glu Leu
                175                 180                 185
```

```
ctt tca tct atg aaa tca cac agt gtt cct gaa gaa ata gat ata gct      808
Leu Ser Ser Met Lys Ser His Ser Val Pro Glu Glu Ile Asp Ile Ala
            190             195                 200 gat aca gta ctc aat gat gat gat att ggt gac agc tgt cat gaa ggc      856
Asp Thr Val Leu Asn Asp Asp Asp Ile Gly Asp Ser Cys His Glu Gly
        205                 210                 215 ttt ctt ctc aat gcc atc agc tca cac ttg caa acc tgt ggc tgt tcc      904
Phe Leu Leu Asn Ala Ile Ser Ser His Leu Gln Thr Cys Gly Cys Ser
        220                 225                 230 gtt gta gta ggt agc agt gca gag aaa gta aat aag ata gtc aga aca      952
Val Val Val Gly Ser Ser Ala Glu Lys Val Asn Lys Ile Val Arg Thr
235             240                 245                 250 tta tgc ctt ttt ctg act cca gca gag aga aaa tgc tcc agg tta tgt     1000
Leu Cys Leu Phe Leu Thr Pro Ala Glu Arg Lys Cys Ser Arg Leu Cys
                255                 260                 265 gaa gca gaa tca tca ttt aaa tat gag tca ggg ctc ttt gta caa ggc     1048
Glu Ala Glu Ser Ser Phe Lys Tyr Glu Ser Gly Leu Phe Val Gln Gly
                270                 275                 280 ctg cta aag gat tca act gga agc ttt gtg ctg cct ttc cgg caa gtc     1096
Leu Leu Lys Asp Ser Thr Gly Ser Phe Val Leu Pro Phe Arg Gln Val
            285                 290                 295 atg tat gct cca tat ccc acc aca cac ata gat gtg gat gtc aat act     1144
Met Tyr Ala Pro Tyr Pro Thr Thr His Ile Asp Val Asp Val Asn Thr
        300                 305                 310 gtg aag cag atg cca ccc tgt cat gaa cat att tat aat cag cgt aga     1192
Val Lys Gln Met Pro Pro Cys His Glu His Ile Tyr Asn Gln Arg Arg
315             320                 325                 330 tac atg aga tcc gag ctg aca gcc ttc tgg aga gcc act tca gaa gaa     1240
Tyr Met Arg Ser Glu Leu Thr Ala Phe Trp Arg Ala Thr Ser Glu Glu
                335                 340                 345 gac atg gct cag gat acg atc atc tac act gac gaa agc ttt act cct     1288
Asp Met Ala Gln Asp Thr Ile Ile Tyr Thr Asp Glu Ser Phe Thr Pro
            350                 355                 360 gat ttg aat att ttt caa gat gtc tta cac aga gac act cta gtg aaa     1336
Asp Leu Asn Ile Phe Gln Asp Val Leu His Arg Asp Thr Leu Val Lys
        365                 370                 375 gcc ttc ctg gat cag gtc ttt cag ctg aaa cct ggc tta tct ctc aga     1384
Ala Phe Leu Asp Gln Val Phe Gln Leu Lys Pro Gly Leu Ser Leu Arg
380             385                 390 agt act ttc ctt gca cag ttt cta ctt gtc ctt cac aga aaa gcc ttg     1432
Ser Thr Phe Leu Ala Gln Phe Leu Leu Val Leu His Arg Lys Ala Leu
395             400                 405                 410 aca cta ata aaa tat ata gaa gac gat acg cag aag gga aaa aag ccc     1480
Thr Leu Ile Lys Tyr Ile Glu Asp Asp Thr Gln Lys Gly Lys Lys Pro
                415                 420                 425 ttt aaa tct ctt cgg aac ctg aag ata gac ctt gat tta aca gca gag     1528
Phe Lys Ser Leu Arg Asn Leu Lys Ile Asp Leu Asp Leu Thr Ala Glu
            430                 435                 440 ggc gat ctt aac ata ata atg gct ctg gct gag aaa att aaa cca ggc     1576
Gly Asp Leu Asn Ile Ile Met Ala Leu Ala Glu Lys Ile Lys Pro Gly
        445                 450                 455 cta cac tct ttt atc ttt gga aga cct ttc tac act agt gtg caa gaa     1624
Leu His Ser Phe Ile Phe Gly Arg Pro Phe Tyr Thr Ser Val Gln Glu
    460                 465                 470 cga gat gtt cta atg act ttt taa atgtgtaact taataagcct attccatcac    1678
Arg Asp Val Leu Met Thr Phe
475             480 aatcatgatc gctggtaaag tagctcagtg gtgtggggaa acgttcccct ggatcatact    1738
```

| | |
|---|---|
| ccagaattct gctctcagca attgcagtta agtaagttac actacagttc tcacaagagc | 1798 |
| ctgtgagggg atgtcaggtg catcattaca ttgggtgtct cttttcctag atttatgctt | 1858 |
| ttgggataca gacctatgtt tacaatataa taaatattat tgctatcttt taaagatata | 1918 |
| ataataggat gtaaacttga ccacaactac tgttttttg aaatacatga ttcatggttt | 1978 |
| acatgtgtca aggtgaaatc tgagttggct tttacagata gttgactttc tatcttttgg | 2038 |
| cattctttgg tgtgtagaat tactgtaata cttctgcaat caactgaaaa ctagagcctt | 2098 |
| taaatgattt caattccaca gaaagaaagt gagcttgaac ataggatgag ctttagaaag | 2158 |
| aaaattgatc aagcagatgt ttaattggaa ttgattatta gatcctactt tgtggattta | 2218 |
| gtccctggga ttcagtctgt agaaatgtct aatagttctc tatagtcctt gttcctggtg | 2278 |
| aaccacagtt agggtgtttt gtttatttta ttgttcttgc tattgttgat attctatgta | 2338 |
| gttgagctct gtaaaaggaa attgtatttt atgttttagt aattgttgcc aacttttaa | 2398 |
| attaattttc attattttg agccaaattg aaatgtgcac ctcctgtgcc ttttttctcc | 2458 |
| ttagaaaatc taattacttg gaacaagttc agatttcact ggtcagtcat tttcatcttg | 2518 |
| ttttcttctt gctaagtctt accatgtacc tgctttggca atcattgcaa ctctgagatt | 2578 |
| ataaaatgcc ttagagaata tactaactaa taagatcttt ttttcagaaa cagaaaatag | 2638 |
| ttccttgagt acttccttct tgcatttctg cctatgtttt tgaagttgtt gctgtttgcc | 2698 |
| tgcaataggc tataaggaat agcaggagaa atttttactga agtgctgttt tcctaggtgc | 2758 |
| tactttggca gagctaagtt atcttttgtt ttcttaatgc gtttggacca ttttgctggc | 2818 |
| tataaaataa ctgattaata taattctaac acaatgttga cattgtagtt acacaaacac | 2878 |
| aaataaatat tttatttaaa attctggaag taatataaaa gggaaaatat atttataaga | 2938 |
| aagggataaa ggtaatagag cccttctgcc ccccacccac caaatttaca caacaaaatg | 2998 |
| acatgttcga atgtgaaagg tcataatagc tttcccatca tgaatcagaa agatgtggac | 3058 |
| agcttgatgt tttagacaac cactgaacta gatgactgtt gtactgtagc tcagtcattt | 3118 |
| aaaaaatata taaatactac cttgtagtgt cccatactgt gttttttaca tggtagattc | 3178 |
| ttatttaagt gctaactggt tattttcttt ggctggttta ttgtactgtt atacagaatg | 3238 |
| taagttgtac agtgaaataa gttattaaag catgtgtaaa cattgttata tatcttttct | 3298 |
| cctaaatgga gaattttgaa taaaatatat ttgaaatttt g | 3339 |

<210> SEQ ID NO 2
<211> LENGTH: 30001
<212> TYPE: DNA
<213> ORGANISM: Homo sapiens

<400> SEQUENCE: 2

| | |
|---|---|
| caaagaaaag ggggaggttt tgttaaaaaa gagaaatgtt acatagtgct ctttgagaaa | 60 |
| attcattggc actattaagg atctgaggag ctggtgagtt tcaactgtg agtgatggtg | 120 |
| gtagataaaa ttagagctgc agcaggtcat tttagcaact attagataaa actggtctca | 180 |
| ggtcacaacg ggcagttgca gcagctggac ttggagagaa ttacactgtg ggagcagtgt | 240 |
| catttgtcct aagtgctttt ctacccccta cccccactat tttagttggg tataaaaaga | 300 |
| atgacccaat ttgtatgatc aactttcaca aagcatagaa cagtaggaaa agggtctgtt | 360 |
| tctgcagaag gtgtagacgt tgagagccat tttgtgtatt tattcctccc tttcttcctc | 420 |
| ggtgaatgat taaaacgttc tgtgtgattt ttagtgatga aaaagattaa atgctactca | 480 |
| ctgtagtaag tgccatctca cacttgcaga tcaaaaggca cacagtttaa aaaaccttg | 540 |

```
tttttttaca catctgagtg gtgtaaatgc tactcatctg tagtaagtgg aatctataca      600
cctgcagacc aaaagacgca aggtttcaaa atctttgtg ttttttacac atcaaacaga      660
atggtacgtt tttcaaaagt taaaaaaaaa caactcatcc acatattgca actagcaaaa      720
atgacattcc ccagtgtgaa aatcatgctt gagagaattc ttacatgtaa aggcaaaatt      780
gcgatgactt tgcaggggac cgtgggattc ccgcccgcag tgccggagct gtcccctacc      840
agggtttgca gtggagtttt gaatgcactt aacagtgtct tacggtaaaa acaaaatttc      900
atccaccaat tatgtgttga gcgcccactg cctaccaagc acaaacaaaa ccattcaaaa      960
ccacgaaatc gtcttcactt tctccagatc cagcagcctc ccctattaag gttcgcacac     1020
gctattgcgc caacgctcct ccagagcggg tcttaagata aagaacagg acaagttgcc      1080
ccgcccatt tcgctagcct cgtgagaaaa cgtcatcgca catagaaaac agacagacgt      1140
aacctacggt gtcccgctag aaagagagg tgcgtcaaac agcgacaagt tccgcccacg      1200
taaaagatga cgcttggtgt gtcagccgtc cctgctgccc ggttgcttct cttttggggg     1260
cggggtctag caagagcagg tgtgggttta ggaggtgtgt gttttttgttt tccccaccct    1320
ctctccccac tacttgctct cacagtactc gctgagggtg aacaagaaaa gacctgataa    1380
agattaacca gaagaaaaca aggagggaaa caaccgcagc ctgtagcaag ctctggaact     1440
caggagtcgc gcgctagggg ccggggccgg ggcggggcg tggtcggggc gggcccgggg     1500
gcgggcccgg ggcggggctg cggttgcggt gcctgcgccc gcggcggcgg aggcgcaggc    1560
ggtggcgagt gggtgagtga ggaggcggca tcctggcggg tggctgtttg gggttcggct    1620
gccgggaaga ggcgcgggta aagcgggg ctctcctcag agctcgacgc attttttactt     1680
tccctctcat ttctctgacc gaagctgggg gtcgggcttt cgcctctagc gactggtgga    1740
attgcctgca tccgggcccc gggcttcccg gcggcggcg cggcggcggc ggcgcaggga     1800
caagggatgg ggatctggcc tcttccttgc tttcccgccc tcagtacccg agctgtctcc    1860
ttcccgggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040
gatgggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggagggtgg ccctttcaga tgcaatcgag attgttaggc     2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tagggggat attaataacc    2640
tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
```

```
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctcttttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat tttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga ttttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg gctaattttt tgtattttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc atttttttttt tcttattctg    4440
ttaggagtga gagtgtaact agcagtataa tagttcaatt ttcacaacgt ggtaaaagtt    4500
tccctataat tcaatcagat tttgctccag ggttcagttc tgttttagga aatactttta    4560
ttttcagttt aatgatgaaa tattagagtt gtaatattgc ctttatgatt atccacctt    4620
ttaacctaaa agaatgaaag aaaaatatgt ttgcaatata atttatggt tgtatgttaa    4680
cttaattcat tatgttggcc tccagttttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920
attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgctttccat cagactgaac tctcttgaca agatgtggat    5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
```

```
ttactttcag tcttagataa caagtcttca attatagtac aatcacacat tgcttaggaa      5340
tgcatcatta ggcgattttg tcattatgca aacatcatag agtgtactta cacaaaccta      5400
gatagtatag cctttatgta cctaggccgt atggtatagt ctgttgctcc taggccacaa      5460
acctgtacaa ctgttactgt actgaatact atagacagtt gtaacacagt ggtaaatatt      5520
tatctaaata tatgcaaaca gagaaaaggt acagtaaaag tatggtataa agataatgg       5580 tatacctgtg taggccactt accacgaatg gagcttgcag gactagaagt tgctctgggt      5640
gagtcagtga gtgagtggtg aattaatgtg aaggcctaga acactgtaca ccactgtaga      5700
ctataaacac agtacgctga agctacacca aatttatctt aacagttttt cttcaataaa      5760
aaattataac ttttaacctt tgtaaacttt ttaatttttt aacttttaaa atacttagct      5820
tgaaacacaa atacattgta tagctataca aaaatatttt ttctttgtat ccttattcta      5880 gaagctttt tctattttct attttaaatt tttttttta cttgttagtc gttttgtta         5940 aaaactaaaa cacacacact ttcacctagg catagacagg attaggatca tcagtatcac      6000
tcccttccac ctcactgcct tccacctcca catcttgtcc cactggaagg ttttaggggg      6060
caataacaca catgtagctg tcacctatga taacagtgct ttctgttgaa tacctcctga      6120
aggacttgcc tgaggctgtt ttacatttaa cttaaaaaaa aaaaagtag aaggagtgca       6180 ctctaaaata acaataaaag gcatagtata gtgaatacat aaaccagcaa tgtagtagtt      6240
tattatcaag tgttgtacac tgtaataatt gtatgtgcta tactttaaat aacttgcaaa      6300
atagtactaa gaccttatga tggttacagt gtcactaagg caatagcata ttttcaggtc      6360
cattgtaatc taatgggact accatcatat atgcagtcta ccattgactg aaacgttaca      6420
tggcacataa ctgtatttgc aagaatgatt tgttttacat taatatcaca taggatgtac      6480 cttttagag tggtatgttt atgtggatta agatgtacaa gttgagcaag gggaccaaga       6540
gccctgggtt ctgtcttgga tgtgagcgtt tatgttcttc tcctcatgtc tgttttctca      6600
ttaaattcaa aggcttgaac gggccctatt tagcccttct gttttctacg tgttctaaat      6660
aactaaagct tttaaattct agccatttag tgtagaactc tctttgcagt gatgaaatgc      6720
tgtattggtt tcttggctag catattaaat attttatct ttgtcttgat acttcaatgt       6780
cgttttaaac atcaggatcg ggcttcagta ttctcataac cagagagttc actgaggata      6840
caggactgtt tgcccatttt ttgttatggc tccagacttg tggtatttcc atgtcttttt      6900 ttttttttt tttttgacc ttttagcggc tttaaagtat ttctgttgtt aggtgttgta        6960
ttacttttct aagattactt aacaaagcac cacaaactga gtggctttaa acaacagcaa      7020
tttattctct cacaattcta gaagctagaa gtccgaaatc aaagtgttga caggggcatg      7080
atcttcaaga gagaagactc tttccttgcc tcttcctggc ttctggtggt taccagcaat      7140
cctgagtgtt cctttcttgc cttgtagttt caacaatcca gtatctgcct tttgtcttca     7200
catggctgtc taccatttgt ctctgtgtct ccaaatctct ctccttataa acacagcagt     7260
tattggatta ggccccactc taatccagta tgaccccatt ttaacatgat tacacttatt     7320
tctagataag gtcacattca cgtacaccaa gggttaggaa ttgaacatat cttttgggg      7380 gacacaattc aacccacaag tgtcagtctc tagctgagcc tttcccttcc tgttttctc     7440 cttttagtt gctatgggtt aggggccaaa tctccagtca tactagaatt gcacatggac      7500
tggatatttg ggaatactgc gggtctattc tatgagcttt agtatgtaac atttaatatc     7560
agtgtaaaga agcccttttt taagttattt ctttgaattt ctaaatgtat gccctgaata     7620
```

```
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttggggtt ttgatggata tctttaaatt    7800
gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg aatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgattttc    8340 agcttattaa tcatgttaac ctatctgttg aaagcttatt ttctggtaca tataaatctt    8400 attttttaa ttatatgcag tgaacatcaa acaataaatg ttatttattt tgcatttacc    8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata cctttttgttt ccctttcatt    8640 gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat ttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc tttttgaaac tatgcagatg ttacattgac tgttttctgt    9180
gaagttatct ttttttcact gcagaataaa ggttgttttg attttatttt gtattgttta    9240
tgagaacatg catttgttgg gttaatttcc taccctgcc cccatttttt ccctaaagta    9300
gaaagtattt ttcttgtgaa ctaaattact acacaagaac atgtctattg aaaaataagc    9360
aagtatcaaa atgttgtggg ttgttttttt aaataaattt tctcttgctc aggaaagaca    9420
agaaaatgtc cagaagatta tcttagaagg cacagagaga atggaagatc aggtatatgc    9480
aaattgcata ctgtcaaatg ttttttctcac agcatgtatc tgtataaggt tgatggctac    9540
atttgtcaag gccttggaga catacgaata agcctttaat ggagctttta tggaggtgta    9600
cagaataaac tggaggaaga tttccatatc ttaaacccaa agagttaaat cagtaaacaa    9660
aggaaaatag taattgcatc tacaaattaa tatttgctcc cttttttttt ctgtttgccc    9720
agaataaatt ttggataact tgttcatagt aaaaataaaa aaaattgtct ctgatatgtt    9780
ctttaaggta ctacttctcg aacctttccc tagaagtagc tgtaacagaa ggagagcata    9840
tgtacccctg aggtatctgt ctggggtgta ggcccaggtc cacacaatat ttcttctaag    9900
tcttatgttt tatcgttaag actcatgcaa tttacatttt attccataac tattttagta    9960
ttaaaatttg tcagtgatat ttcttaccct ctcctctagg aaaatgtgcc atgtttatcc   10020
```

```
cttggctttg aatgcccctc aggaacagac actaagagtt tgagaagcat ggttacaagg    10080
gtgtggcttc ccctgcggaa actaagtaca gactatttca ctgtaaagca gagaagttct    10140
tttgaaggag aatctccagt gaagaaagag ttcttcactt ttacttccat ttcctcttgt    10200
gggtgaccct caatgctcct tgtaaaactc aatatttta aacatggctg ttttgccttt     10260
ctttgcttct ttttagcatg aatgagacag atgatacttt aaaaagtaa ttaaaaaaaa     10320
aaacttgtga aaatacatgg ccataataca gaacccaata caatgatctc ctttaccaaa    10380
ttgttatgtt tgtactttg tagatagctt tccaattcag agacagttat tctgtgtaaa     10440
ggtctgactt aacaagaaaa gatttccctt tacccaaaga atcccagtcc ttatttgctg    10500
gtcaataagc agggtcccca ggaatggggt aactttcagc accctctaac ccactagtta    10560
ttagtagact aattaagtaa acttatcgca agttgaggaa acttagaacc aactaaaatt    10620
ctgcttttac tgggattttg tttttcaaa ccagaaacct ttacttaagt tgactactat     10680
taatgaattt tggtctctct tttaagtgct cttcttaaaa atgttatctt actgctgaga    10740
agttcaagtt tgggaagtac aaggaggaat agaaacttaa gagattttct tttagagcct    10800
cttctgtatt tagccctgta ggattttttt tttttttttt tttttggtg ttgttgagct     10860
tcagtgaggc tattcattca cttatactga taatgtctga gatactgtga atgaaatact    10920
atgtatgctt aaacctaaga ggaaatattt tcccaaaatt attcttcccg aaaaggagga    10980
gttgcctttt gattgagttc ttgcaaatct cacaacgact ttattttgaa caatactgtt    11040
tggggatgat gcattagttt gaaacaactt cagttgtagc tgtcatctga taaaattgct    11100
tcacagggaa ggaaatttaa cacggatcta gtcattattc ttgttagatt gaatgtgtga    11160
attgtaattg taaacaggca tgataattat tactttaaaa actaaaaaca gtgaatagtt    11220
agttgtggag gttactaaag gatggttttt ttttaaataa aactttcagc attatgcaaa    11280
tgggcatatg gcttaggata aaacttccag aagtagcatc acatttaaat tctcaagcaa    11340
cttaataata tggggctctg aaaaactggt taaggttact ccaaaaatgg ccctgggtct    11400
gacaaagatt ctaacttaaa gatgcttatg aagactttga gtaaaatcat ttcataaaat    11460
aagtgaggaa aaacaactag tattaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc    11640
catatttgag acactttaca tttgtgatgt gttatactga attttcagtt tgattctata    11700
gactacaaat ttcaaaatta caatttcaag atgtaataag tagtaaatatc ttgaaatagc    11760
tctaaaggga atttttctgt tttattgatt cttaaaatat atgtgctgat tttgatttgc    11820
atttgggtag attatacttt tatgagtatg gaggttaggt attgattcaa gttttcctta    11880
cctatttggt aaggatttca aagtctttt gtgcttggtt ttcctcattt ttaaatatga    11940
aatatattga tgacctttaa caatttttt ttatctcaaa ttttaaagga gatcttttct    12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atgcgaaac cccgtctcta ctaaaaatac aaaaatcagc cgggcatggt     12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aagtgagct ttggattgca     12360
```

```
tataaatcct ttagacatgt agtagacttg tttgatactg tgtttgaaca aattacgaag  12420
tattttcatc aaagaatgtt attgtttgat gttatttta tttttattg cccagcttct     12480 ctcatattac gtgattttct tcacttcatg tcactttatt gtgcagggtc agagtattat   12540
tccaatgctt actggagaag tgattcctgt aatggaactg ctttcatcta tgaaatcaca   12600
cagtgttcct gaagaaatag atgtaagttt aaatgagagc aattatacac tttatgagtt   12660
ttttggggtt atagtattat tatgtatatt attaatattc taattttaat agtaaggact   12720
ttgtcataca tactattcac atacagtatt agccactta gcaataagc acacacaaaa     12780 tcctggattt tatggcaaaa cagaggcatt tttgatcagt gatgacaaaa ttaaattcat   12840
tttgtttatt tcattacttt tataattcct aaaagtggga ggatcccagc tcttatagga   12900
gcaattaata tttaatgtag tgtctttga aacaaaactg tgtgccaaag tagtaaccat    12960
taatggaagt ttacttgtag tcacaaattt agtttcctta atcatttgtt gaggacgttt   13020
tgaatcacac actatgagtg ttaagagata cctttaggaa actattcttg ttgttttctg   13080
attttgtcat ttaggttagt ctcctgattc tgacagctca gaagaggaag ttgttcttgt   13140
aaaaattgtt taacctgctt gaccagcttt cacatttgtt cttctgaagt ttatggtagt   13200
gcacagagat tgttttttgg gggagtcttga ttctcggaaa tgaaggcagt gtgttatatt   13260
gaatccagac ttccgaaaac ttgtatatta aaagtgttat ttcaacacta tgttacagcc   13320
agactaattt ttttattttt tgatgcattt tagatagctg atacagtact caatgatgat   13380
gatattggtg acagctgtca tgaaggcttt cttctcaagt aagaattttt cttttcataa   13440
aagctggatg aagcagatac catcttatgc tcacctatga caagatttgg aagaaagaaa   13500
ataacagact gtctacttag attgttctag ggacattacg tatttgaact gttgcttaaa   13560
tttgtgttat ttttcactca ttatatttct atatatattt ggtgttattc catttgctat   13620
ttaaagaaac cgagtttcca tcccagacaa gaaatcatgg cccccttgctt gattctggtt   13680 tcttgtttta cttctcatta aagctaacag aatcctttca tattaagttg tactgtagat   13740
gaacttaagt tatttaggcg tagaacaaaa ttattcatat ttatactgat cttttttccat  13800 ccagcagtgg agtttagtac ttaagagttt gtgcccttaa accagactcc ctggattaat   13860
gctgtgtacc cgtgggcaag gtgcctgaat tctctataca cctatttcct catctgtaaa   13920
atggcaataa tagtaatagt acctaatgtg taggggttgtt ataagcattg agtaagataa   13980
ataatataaa gcacttagaa cagtgcctgg aacataaaaa cacttaataa tagctcatag    14040
ctaacatttc ctatttacat ttcttctaga aatagccagt atttgttgag tgcctacatg    14100
ttagttcctt tactagttgc tttacatgta ttatcttata ttctgtttta aagtttcttc    14160
acagttacag atttttcatga aattttactt ttaataaaag agaagtaaaa gtataaagta   14220
ttcactttta tgttcacagt cttttccttt aggctcatga tggagtatca gaggcatgag   14280
tgtgtttaac ctaagagcct taatggcttg aatcagaagc actttagtcc tgtatctgtt    14340
cagtgtcagc ctttcataca tcatttttaaa tcccatttga ctttaagtaa gtcacttaat   14400
ctctctacat gtcaatttct tcagctataa aatgatggta tttcaataaa taaatacatt    14460
aattaaatga tattatactg actaattggg ctgttttaag gctcaataag aaaatttctg    14520
tgaaaggtct ctagaaaatg taggttccta tacaaataaa agataacatt gtgcttatag   14580
cttcggtgtt tatcatataa agctattctg agttatttga agagctcacc tactttttt    14640 tgttttagt ttgttaaatt gttttatagg caatgttttt aatctgtttt ctttaactta    14700
cagtgccatc agctcacact tgcaaacctg tggctgttcc gttgtagtag gtagcagtgc   14760
```

```
agagaaagta aataaggtag tttattttat aatctagcaa atgatttgac tctttaagac   14820
tgatgatata tcatggattg tcatttaaat ggtaggttgc aattaaaatg atctagtagt   14880
ataaggaggc aatgtaatct catcaaattg ctaagacacc ttgtggcaac agtgagtttg   14940
aaataaactg agtaagaatc atttatcagt ttattttgat agctcggaaa taccagtgtc   15000
agtagtgtat aaatggtttt gagaatatat taaaatcaga tatataaaaa aaattactct   15060
tctatttccc aatgttatct ttaacaaatc tgaagatagt catgtacttt tggtagtagt   15120
tccaaagaaa tgttatttgt ttattcatct tgatttcatt gtcttcgctt tccttctaaa   15180
tctgtccctt ctagggagct attgggatta agtggtcatt gattattata ctttattcag   15240
taatgtttct gaccctttcc ttcagtgcta cttgagttaa ttaaggatta atgaacagtt   15300
acatttccaa gcattagcta ataaactaaa ggattttgca cttttcttca ctgaccatta   15360
gttagaaaga gttcagagat aagtatgtgt atctttcaat ttcagcaaac ctaattttt   15420 aaaaaaagtt ttacatagga aatatgttgg aaatgatact ttacaaagat attcataatt   15480
tttttttgta atcagctact ttgtatattt acatgagcct taatttatat ttctcatata   15540
accatttatg agagcttagt atacctgtgt cattatattg catctacgaa ctagtgacct   15600
tattccttct gttacctcaa acaggtggct ttccatctgt gatctccaaa gccttaggtt   15660
gcacagagtg actgccgagc tgctttatga agggagaaag gctccatagt tggagtgttt   15720
tttttttttt ttttaaacat ttttcccatc ctccatcctc ttgagggaga atagcttacc   15780
ttttatcttg ttttaatttg agaaagaagt tgccaccact ctaggttgaa aaccactcct   15840
ttaacataat aactgtggat atggtttgaa tttcaagata gttacatgcc ttttattt   15900 tcctaataga gctgtaggtc aaatattatt agaatcagat ttctaaatcc cacccaatga   15960
cctgcttatt ttaaatcaaa ttcaataatt aattctcttc tttttggagg atctggacat   16020
tctttgatat ttcttacaac gaatttcatg tgtagaccca ctaaacagaa gctataaaag   16080
ttgcatggtc aaataagtct gagaaagtct gcagatgata taattcacct gaagagtcac   16140
agtatgtagc caaatgttaa aggttttgag atgccataca gtaaatttac caagcatttt   16200
ctaaatttat ttgaccacag aatccctatt ttaagcaaca actgttacat cccatggatt   16260
ccaggtgact aaagaatact tatttcttag gatatgtttt attgataata acaattaaaa   16320
tttcagatat ctttcataag caaatcagtg gtcttttac ttcatgtttt aatgctaaaa   16380
tattttcttt tatagatagt cagaacatta tgccttttc tgactccagc agagagaaaa   16440
tgctccaggt tatgtgaagc agaatcatca tttaaatatg agtcagggct ctttgtacaa   16500
ggcctgctaa aggtatagtt tctagttatc acaagtgaaa ccacttttct aaaatcattt   16560
ttgagactct ttatagacaa atcttaaata ttagcattta atgtatctca tattgacatg   16620
cccagagact gacttccttt acacagttct gcacatagac tatatgtctt atggatttat   16680
agttagtatc atcagtgaaa caccatagaa taccctttgt gttccaggtg ggtccctgtt   16740
cctacatgtc tagcctcagg acttttttt ttttaacaca tgcttaaatc aggttgcaca   16800
tcaaaaataa gatcatttct ttttaactaa atagatttga attttattga aaaaaatt   16860 taaacatctt taagaagctt ataggattta agcaattcct atgtatgtgt actaaaatat   16920
atatatttct atatataata tatattagaa aaaattgta ttttcttt atttgagtct   16980 actgtcaagg agcaaaacag agaaatgtaa attagcaatt atttataata cttaaaggga   17040
agaaagttgt tcaccttgtt gaatctatta ttgttatttc aattatagtc ccaagacgtg   17100
```

```
aagaaatagc tttcctaatg gttatgtgat tgtctcatag tgactacttt cttgaggatg   17160
tagccacggc aaaatgaaat aaaaaaattt aaaaattgtt gcaaatacaa gttatattag   17220
gcttttgtgc attttcaata atgtgctgct atgaactcag aatgatagta tttaaatata   17280
gaaactagtt aaaggaaacg tagtttctat ttgagttata catatctgta aattagaact   17340
tctcctgtta aaggcataat aaagtgctta atacttttgt ttcctcagca ccctctcatt   17400
taattatata attttagttc tgaaagggac ctataccaga tgcctagagg aaatttcaaa   17460
actatgatct aatgaaaaaa tatttaatag ttctccatgc aaatacaaat catatagttt   17520
tccagaaaat acctttgaca ttatacaaag atgattatca cagcattata atagtaaaaa   17580
aatggaaata gcctctttct tctgttctgt tcatagcaca gtgcctcata cgcagtaggt   17640
tattattaca tggtaactgg ctaccccaac tgattaggaa agaagtaaat ttgttttata   17700
aaaatacata ctcattgagg tgcatagaat aattaagaaa ttaaaagaca cttgtaattt   17760
tgaatccagt gaatacccac tgttaatatt tggtatatct cttctagtc ttttttccc   17820 ttttgcatgt attttcttta agactcccac ccccactgga tcatctctgc atgttctaat   17880
ctgctttttt cacagcagat tctaagcctc tttgaatatc aacacaaact tcaacaactt   17940
catctataga tgccaaataa taaattcatt tttatttact taaccacttc ctttggatgc   18000
ttaggtcatt ctgatgtttt gctattgaaa ccaatgctat actgaacact tctgtcacta   18060
aaactttgca cacactcatg aatagcttct taggataaat ttttagagat ggatttgcta   18120
aatcagagac catttttaa aattaaaaaa caattattca tatcgtttgg catgtaagac   18180
agtaaatttt cctttatttt tgacaggatt caactgaaag ctttgtgctg cctttccggc   18240
aagtcatgta tgctccatat cccaccacac acatagatgt ggatgtcaat actgtgaagc   18300
agatgccacc ctgtcatgaa catatttata atcagcgtag atacatgaga tccgagctga   18360
cagccttctg gagagccact tcagaagaag acatggctca ggatacgatc atctacactg   18420
acgaaagctt tactcctgat ttgtacgtaa tgctctgcct gctggtactg tagtcaagca   18480
atatgaaatt gtgtctttta cgaataaaaa caaaacagaa gttgcattta aaaagaaaga   18540
aatattacca gcagaattat gcttgaagaa acatttaatc aagcattttt tcttaaatg   18600 ttcttctttt tccatacaat tgtgtttacc ctaaaatagg taagattaac ccttaaagta   18660
aatatttaac tatttgttta ataaatatat attgagctcc taggcactgt tctaggtacc   18720
gggcttaata gtggccaacc agacagcccc agccccagcc cctacattgt gtatagtcta   18780
ttatgtaaca gttattgaat ggacttatta acaaaaccaa agaagtaatt ctaagtctttt  18840 ttttttcttga catatgaata taaaatacag caaaactgtt aaaatatatt aatggaacat   18900
tttttacttt tgcattttat attgttattc acttcttatt tttttttaaa aaaaaaagcc   18960
tgaacagtaa attcaaaagg aaaagtaatg ataattaatt gttgagcatg gacccaactt   19020
gaaaaaaaaa atgatgatga taaatctata atcctaaaac cctaagtaaa cacttaaaag   19080
atgttctgaa atcaggaaaa gaattatagt atactttgt gtttctcttt tatcagttga    19140
aaaaaggcac agtagctcat gcctgtaaga acagagcttt gggagtgcaa ggcaggcgga   19200
tcacttgagg ccaggagttc cagaccagcc tgggcaacat agtgaaaccc catctctaca   19260
aaaaataaaa aagaattatt ggaatgtgtt tctgtgtgcc tgtaatccta gctattccga   19320
aagctgaggc aggaggatct tttgagccca ggagtttgag gttacaggga gttatgatgt   19380
gccagtgtac tccagcctgg ggaacaccga gactctgtct tatttaaaaa aaaaaaaaaa   19440
aaaatgcttg caataatgcc tggcacatag aaggtaacag taagtgttaa ctgtaataac   19500
```

```
ccaggtctaa gtgtgtaagg caatagaaaa attggggcaa ataagcctga cctatgtatc   19560
tacagaatca gtttgagctt aggtaacaga cctgtggagc accagtaatt acacagtaag   19620
tgttaaccaa aagcatagaa taggaatatc ttgttcaagg gacccccagc cttatacatc   19680
tcaaggtgca gaaagatgac ttaatatagg acccatttt tcctagttct ccagagtttt   19740
tattggttct tgagaaagta gtaggggaat gttttagaaa atgaattggt ccaactgaaa   19800
ttacatgtca gtaagttttt atatattggt aaatttagt agacatgtag aagttttcta   19860
attaatctgt gccttgaaac attttctttt ttcctaaagt gcttagtatt ttttccgttt   19920
tttgattggt tacttgggag ctttttttgag gaaatttagt gaactgcaga atgggtttgc   19980
aaccatttgg tattttgtt ttgtttttta gaggatgtat gtgtatttta acatttctta   20040 atcatttta gccagctatg tttgttttgc tgatttgaca aactacagtt agacagctat   20100
tctcattttg ctgatcatga caaaataata tcctgaattt ttaaattttg catccagctc   20160
taaattttct aaacataaaa ttgtccaaaa aatagtattt tcagccacta gattgtgtgt   20220
taagtctatt gtcacagagt cattttactt ttaagtatat gttttacat gttaattatg   20280 tttgttattt ttaattttaa ctttttaaaa taattccagt cactgccaat acatgaaaaa   20340
ttggtcactg gaattttttt tttgacttt attttaggtt catgtgtaca tgtgcaggtg   20400
tgttatacag gtaaattgcg tgtcatgagg gtttggtgta caggtgattt cattacccag   20460
gtaataagca tagtacccaa taggtagttt tttgatcctc acccttctcc caccctcaag   20520
taggccctgg tgttgctgtt tccttctttg tgtccatgta tactcagtgt ttagctccca   20580
cttagaagtg agaacatgcg gtagttggtt ttctgttcct ggattagttc acttaggata   20640
atgacctcta gctccatctg gttttttatgg ctgcatagta ttccatggtg tatatgtatc   20700
acattttctt tatccagtct accattgata ggcatttagg ttgattccct gtctttgtta   20760
tcatgaatag tgctgtgatg aacatacaca tgcatgtgtc tttatggtag aaaatttgt   20820 attcctttag gtacatatag aataatgggg ttgctagggt gaatggtagt tctattttca   20880
gttatttgag aaatcttcaa actgcttttc ataatagcta aactaattta cagtcccgcc   20940
agcagtgtat aagtgttccc ttttctccac aaccttgcca acatctgtga ttttttgact   21000
ttttaataat agccattcct agagaattga tttgcaattc tctattagtg atattaagca   21060 tttttcata tgctttttag ctgtctgtat atattcttct gaaaattttt catgtccttt   21120
gcccagtttg tagtggggtg ggttgttttt tgcttgttaa ttagtttta gttccttcca   21180 gattctgcat atcccttgt tggatacatg gtttgcagat attttctcc cattgtgtag   21240 gttgtctttt actctgttga tagtttcttt tgccatgcag gagctcgtta ggtcccattt   21300
gtgtttgttt ttgttgcagt tgcttttggc gtcttcatca taaatctgt gccagggcct   21360 atgtccagaa tggtatttcc taggttgtct tccagggttt ttacaatttt agattttacg   21420
tttatgtctt taatccatct tgagttgatt tttgtatatg gcacaaggaa ggggtccagt   21480
ttcactccaa ttcctatggc tagcaattat cccagcacca tttattgaat acggagtcct   21540
ttccccattg cttgtttttt gtcaactttg ttgaagatca gatggttgta agtgtgtggc   21600
tttatttctt ggctctctat tctccattgg tctatgtgtc tgttttata acagtaccct   21660 gctgttcagg ttcctatagc cttttagtat aaaatcggct aatgtgatgc ctccagcttt   21720 gttcttttg cttaggattg ctttggctat ttgggctcct ttttgggtcc atattaattt   21780
taaaacagtt ttttctggtt ttgtgaagga tatcattggt agtttatagg aatagcattg   21840
```

```
aatctgtaga ttgctttggg cagtatggcc attttaacaa tattaattct tcctatctat   21900
gaatatggaa tgttttttcca tgtgtttgtg tcatctcttt atacctgatg tataaagaaa   21960
agctggtatt attcctactc aatctgttcc aaaaaattga ggaggaggaa ctcttcccta   22020
atgaggccag catcattctg ataccaaaac ctggcagaga cacaacgaaa aaagaaaaac   22080
ttcaggccaa tatccttgat gaatatagat gcaaaatcc tcaacaaaat actagcaaac   22140
caaatccagc agcacatcaa aaagctgatc tactttgatc aagtaggctt tatccctggg   22200
atgcaaggtt ggttcaacat acacaaatca ataagtgtga ttcatcacat aaacagagct   22260
aaaaacaaaa accacaagat tatctcaata ggtagagaaa aggttgtcaa taaaatttaa   22320
catcctccat gttaaaaacc ttcagtaggt caggtgtagt gactcacacc tgtaatccca   22380
gcactttggg aggccaaggc gggcatatct cttaagccca ggagttcaag acgagcctag   22440
gcagcatggt gaaaccccat ctctacaaaa aaaaaaaaaa aaaaaaatta gcttggtatg   22500
gtgacatgca cctatagtcc cagctattca ggaggttgag gtgggaggat tgtttgagcc   22560
cgggaggcag aggttggcag cgagctgaga tcatgccacc gcactccagc ctgggcaacg   22620
gagtgagacc ctgtctcaaa aagaaaaat cacaaacaat cctaaacaaa ctaggcattg   22680
aaggaacatg cctcaaaaaa ataagaacca tctatgacag acccatagcc aatatcttac   22740
caaatgggca aaagctggaa gtattctcct tgagaaccgt aacaagacaa ggatgtccac   22800
tctcaccact cctttttcagc atagttctgg aagtcctagc cagagcaatc aggaaagaga   22860
aagaaagaaa gacattcaga taggaagaga agaagtcaaa ctatttctgt ttgcaggcag   22920
tataattctg tacctagaaa atctcatagt ctctgcccag aaactcctaa atctgttaaa   22980
aatttcagca agttttggc attctctata ctccaacacc ttccaaagtg agagcaaaat   23040
caagaacaca gtcccattca caatagccgc aaaacgaata aaatacctag gaatccagct   23100
aaccagggag gtgaaagatc tctatgagaa ttacaaaaca ctgctgaaag aaatcagaga   23160
tgacacaaac aaatggaaat gttcttttt aacaccttgc tttatctaat tcacttatga   23220
tgaagatact cattcagtgg aacaggtata ataagtccac tcgattaaat ataagcctta   23280
ttctctttcc agagcccaag aagggcact atcagtgccc agtcaataat gacgaaatgc   23340
taatattttt cccctttacg gtttctttct tctgtagtgt ggtacactcg tttcttaaga   23400
taaggaaact tgaactacct tcctgtttgc ttctacacat acccattctc ttttttttgcc   23460
actctggtca ggtataggat gatccctacc actttcagtt aaaaactcct cctcttacta   23520
aatgttctct taccctctgg cctgagtaga acctagggaa aatggaagag aaaaagatga   23580
aagggaggtg gggcctggga agggaataag tagtcctgtt tgtttgtgtg tttgctttag   23640
cacctgctat atcctaggtg ctgtgttagg cacacattat tttaagtggc cattatatta   23700
ctactactca ctctggtcgt tgccaaggta ggtagtactt tcttggatag ttggttcatg   23760
ttacttacag atggtgggct tgttgaggca aacccagtgg ataatcatcg gagtgtgttc   23820
tctaatctca ctcaaatttt tcttcacatt ttttggtttg ttttggtttt tgatggtagt   23880
ggcttatttt tgttgctggt ttgtttttttg tttttttttg agatggcaag aattggtagt   23940
tttatttatt aattgcctaa gggtctctac ttttttttaaa agatgagagt agtaaaatag   24000
attgatagat acatacatac ccttactggg gactgcttat attctttaga gaaaaaatta   24060
catattagcc tgacaaacac cagtaaaatg taaatatatc cttgagtaaa taatgaatg   24120
tatatttttgt gtctccaaat atatatatct atattcttac aaatgtgttt atatgtaata   24180
tcaatttata agaacttaaa atgttggctc aagtgaggga ttgtggaagg tagcattata   24240
```

```
tggccatttc aacatttgaa ctttttcctt ttcttcattt tcttcttttc ttcaggaata   24300
tttttcaaga tgtcttacac agagacactc tagtgaaagc cttcctggat caggtaaatg   24360
ttgaacttga gattgtcaga gtgaatgata tgacatgttt tcttttttaa tatatcctac   24420
aatgcctgtt ctatatattt atattcccct ggatcatgcc ccagagttct gctcagcaat   24480
tgcagttaag ttagttacac tacagttctc agaagagtct gtgagggcat gtcaagtgca   24540
tcattacatt ggttgcctct tgtcctagat ttatgcttcg ggaattcaga cctttgttta   24600
caatataata aatattattg ctatctttta aagatataat aataagatat aaagttgacc   24660
acaactactg tttttgaaa catagaattc ctggtttaca tgtatcaaag tgaaatctga   24720
cttagctttt acagatataa tatatacata tatatatcct gcaatgcttg tactatatat   24780
gtagtacaag tatatatata tgtttgtgtg tgtatatata tatagtacga gcatatatac   24840
atattaccag cattgtagga tatatatatg tttatatatt aaaaaaaagt tataaactta   24900
aaaccctatt atgttatgta gagtatatgt tatatatgat atgtaaaata tataacatat   24960
actctatgat agagtgtaat atatttttta tatatatttt aacatttata aaatgataga   25020
attaagaatt gagtcctaat ctgttttatt aggtgctttt tgtagtgtct ggtctttcta   25080
aagtgtctaa atgattttc cttttgactt attaatgggg aagagcctgt atattaacaa   25140
ttaagagtgc agcattccat acgtcaaaca acaaacattt taattcaagc attaacctat   25200
aacaagtaag tttttttttt tttttgaga agggaggtt gtttatttgc ctgaaatgac   25260
tcaaaaatat ttttgaaaca tagtgtactt atttaaataa catctttatt gtttcattct   25320 tttaaaaat atctacttaa ttacacagtt gaaggaaatc gtagattata tggaacttat   25380
ttcttaatat attacagttt gttataataa cattctgggg atcaggccag gaaactgtgt   25440
catagataaa gctttgaaat aatgagatcc ttatgtttac tagaaatttt ggattgagat   25500
ctatgaggtc tgtgacatat tgcgaagttc aaggaaaatt cgtaggcctg gaatttcatg   25560
cttctcaagc tgacataaaa tccctcccac tctccacctc atcatatgca cacattctac   25620
tcctacccac ccactccacc ccctgcaaaa gtacaggtat atgaatgtct caaaaccata   25680
ggctcatctt ctaggagctt caatgttatt tgaagatttg ggcagaaaaa attaagtaat   25740
acgaaataac ttatgtatga gttttaaaag tgaagtaaac atggatgtat tctgaagtag   25800
aatgcaaaat ttgaatgcat ttttaaagat aaattagaaa acttctaaaa actgtcagat   25860
tgtctgggcc tggtggctta tgcctgtaat cccagcactt tgggagtccg aggtgggtgg   25920
atcacaaggt caggagatcg agaccatcct gccaacatgg tgaaaccccg tctctactaa   25980
gtatacaaaa attagctggg cgtggcagcg tgtgcctgta atcccagcta cctgggaggc   26040
tgaggcagga gaatcgcttg aacccaggag gtgtaggttg cagtgagtca agatcgcgcc   26100
actgcacttt agcctggtga cagagctaga ctccgtctca aaaaaaaaa aaaatatcag   26160 attgttccta cacctagtgc ttctatacca cactcctgtt aggggcatc agtggaaatg   26220 gttaaggaga tgtttagtgt gtattgtctg ccaagcactg tcaacactgt catagaaact   26280
tctgtacgag tagaatgtga gcaaattatg tgttgaaatg gttcctctcc ctgcaggtct   26340
ttcagctgaa acctggctta tctctcagaa gtactttcct tgcacagttt ctacttgtcc   26400
ttcacagaaa agccttgaca ctaataaaat atatagaaga cgatacgtga gtaaaactcc   26460
tacacggaag aaaaaccttt gtacattgtt ttttgttttt gtttcctttg tacattttct   26520
atatcataat ttttgcgctt ctttttttttt tttttttttt tttttttcca ttatttttag   26580
```

```
gcagaaggga aaaaagccct ttaaatctct tcggaacctg aagatagacc ttgatttaac    26640
agcagagggc gatcttaaca taataatggc tctggctgag aaaattaaac caggcctaca    26700 ctctttatc tttggaagac ctttctacac tagtgtgcaa gaacgagatg ttctaatgac     26760
tttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatcttttaa agatataata ataggatgta aacttgacca    27060
caactactgt ttttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctactttgt ggatttagtc cctgggattc agtctgtaga    27360
aatgtctaat agttctctat agtccttgtt cctggtgaac cacagttagg gtgttttgtt    27420
tattttattg ttcttgctat tgttgatatt ctatgtagtt gagctctgta aaaggaaatt    27480 gtatttatg ttttagtaat tgttgccaac tttttaaatt aattttcatt attttgagc     27540 caaattgaaa tgtgcacctc ctgtgccttt tttctcctta gaaatctaa ttacttggaa     27600 caagttcaga tttcactggt cagtcatttt catcttgttt tcttcttgct aagtcttacc    27660
atgtacctgc tttggcaatc attgcaactc tgagattata aaatgcctta gagaatatac    27720
taactaataa gatctttttt tcagaaacag aaaatagttc cttgagtact tccttcttgc    27780
atttctgcct atgtttttga agttgttgct gtttgcctgc aataggctat aaggaatagc    27840
aggagaaatt ttactgaagt gctgttttcc taggtgctac tttggcagag ctaagttatc    27900
ttttgttttc ttaatgcgtt tggaccattt tgctggctat aaaataactg attaatataa    27960
ttctaacaca atgttgacat tgtagttaca caaacacaaa taaatatttt atttaaaatt    28020
ctggaagtaa tataaaaggg aaaatatatt tataagaaag ggataaaggt aatagagccc    28080
ttctgccccc cacccaccaa atttacacaa caaaatgaca tgttcgaatg tgaaaggtca    28140
taatagcttt cccatcatga atcagaaaga tgtggacagc ttgatgtttt agacaaccac    28200
tgaactagat gactgttgta ctgtagctca gtcatttaaa aaatatataa atactacctt    28260
gtagtgtccc atactgtgtt ttttacatgg tagattctta tttaagtgct aactggttat    28320
tttctttggc tggtttattg tactgttata cagaatgtaa gttgtacagt gaaataagtt    28380
attaaagcat gtgtaaacat tgttatatat cttttctcct aaatggagaa ttttgaataa    28440
aatatatttg aaattttgcc tctttcagtt gttcattcag aaaaaaatac tatgatattt    28500
gaagactgat cagcttctgt tcagctgaca gtcatgctgg atctaaactt ttttttaaaat   28560 taattttgtc ttttcaaaga aaaatatttt aaagaagctt tataatataa tcttatgtta    28620
aaaaaacttt ctgcttaact ctctggattt cattttgatt tttcaaatta tatattaata    28680
tttcaaatgt aaaatactat ttagataaat tgttttttaaa cattcttatt attataatat   28740
taatataacc taaactgaag ttattcatcc caggtatcta atacatgtat ccaaagtaaa    28800
aatccaagga atctgaacac tttcatctgc aaagctagga ataggtttga cattttcact    28860
ccaagaaaaa gttttttttt gaaaatagaa tagttgggat gagaggtttc tttaaaagaa    28920
gactaactga tcacattact atgattctca aagaagaaac caaaacttca tataatacta    28980
```

| | | | | |
|---|---|---|---|---|
| taaagtaaat | ataaaatagt | tccttctata | gtatatttct | ataatgctac agtttaaaca 29040 |
| gatcactctt | atataatact | attttgattt | tgatgtagaa | ttgcacaaat tgatatttct 29100 |
| cctatgatct | gcagggtata | gcttaaagta | acaaaaacag | tcaaccacct ccatttaaca 29160 |
| cacagtaaca | ctatgggact | agtttttatta | cttccatttt | acaaatgagg aaactaaagc 29220 |
| ttaaagatgt | gtaatacacc | gcccaaggtc | acacagctgg | taaaggtgga tttcatccca 29280 |
| gacagttaca | gtcattgcca | tgggcacagc | tcctaactta | gtaactccat gtaactggta 29340 |
| ctcagtgtag | ctgaattgaa | aggagagtaa | ggaagcaggt | tttacaggtc tacttgcact 29400 |
| attcagagcc | cgagtgtgaa | tccctgctgt | gctgcttgga | gaagttactt aacctatgca 29460 |
| aggttcattt | tgtaaatatt | ggaaatggag | tgataatacg | tacttcacca gaggatttaa 29520 |
| tgagaccttà | tacgatcctt | agttcagtac | ctgactagtg | cttcataaat gcttttcat 29580 |
| ccaatctgac | aatctccagc | ttgtaattgg | ggcatttaga | acatttaata tgattattgg 29640 |
| catggtaggt | taaagctgtc | atcttgctgt | tttctatttg | ttcttttgt tttctccta 29700 |
| cttttggatt | tttttattct | actatgtctt | ttctattgtc | ttattaacta tactctttga 29760 |
| tttattttag | tggttgtttt | agggttatac | ctctttctaa | tttaccagtt tataaccagt 29820 |
| ttatatacta | cttgacatat | agcttaagaa | acttactgtt | gttgtcttt tgctgttatg 29880 |
| gtcttaacgt | ttttatttct | acaaacatta | taaactccac | actttattgt tttttaattt 29940 |
| tacttataca | gtcaattatc | ttttaaagat | atttaaatat | aaacattcaa aacaccccaa 30000 |
| t | | | | 30001 |

<210> SEQ ID NO 3
<211> LENGTH: 1031
<212> TYPE: DNA
<213> ORGANISM: Homo sapiens

<400> SEQUENCE: 3

| | | | | |
|---|---|---|---|---|
| attcccggga | tacgtaacct | acggtgtccc | gctaggaaag | agaggtgcgt caaacagcga 60 |
| caagttccgc | ccacgtaaaa | gatgacgctt | ggtgtgtcag | ccgtccctgc tgcccggttg 120 |
| cttctctttt | gggggcgggg | tctagcaaga | gcaggtgtgg | gtttaggaga tatctccgga 180 |
| gcatttggat | aatgtgacag | ttggaatgca | gtgatgtcga | ctctttgccc accgccatct 240 |
| ccagctgttg | ccaagacaga | gattgcttta | agtggcaaat | cacctttatt agcagctact 300 |
| tttgcttact | gggacaatat | tcttggtcct | agagtaaggc | acatttgggc tccaaagaca 360 |
| gaacaggtac | ttctcagtga | tggagaaata | acttttcttg | ccaaccacac tctaaatgga 420 |
| gaaatccttc | gaaatgcaga | gagtggtgct | atagatgtaa | agttttttgt cttgtctgaa 480 |
| aagggagtga | ttattgtttc | attaatcttt | gatggaaact | ggaatgggga tcgcagcaca 540 |
| tatggactat | caattatact | tccacagaca | gaacttagtt | tctacctccc acttcataga 600 |
| gtgtgtgttg | atagattaac | acatataatc | cggaaaggaa | gaatatggat gcataaggaa 660 |
| agacaagaaa | aatgtccaga | agattatctt | agaaggcaca | gagagaatgg aagatcaggg 720 |
| tcagagtatt | attccaatgc | ttactggaga | agtgattcct | gtaatggaaa ctgctttcct 780 |
| ctatgaaatt | ccccccgggtt | cctggaggaa | atagatatag | gctgatacag ttacccaatg 840 |
| atggatgaat | attggggggac | cgcctggtca | ttgaaaggct | ttcttttctc caggaaagaa 900 |
| attttttcc | ttttccataa | aaagcttggg | aatggaagac | aacaattccc attctttttt 960 |
| tgcgttccac | ccctatgtga | caacagaaat | ttttggggaa | acaacaacga aaaaatttta 1020 | tcccgcgcgc a                                                          1031

<210> SEQ ID NO 4
<211> LENGTH: 3244
<212> TYPE: DNA
<213> ORGANISM: Homo sapiens
<220> FEATURE:
<221> NAME/KEY: CDS
<222> LOCATION: (108)..(1553)

<400> SEQUENCE: 4
gggcggggct gcggttgcgg tgcctgcgcc cgcggcggcg gaggcgcagg cggtggcgag    60
tggatatctc cggagcattt ggataatgtg acagttggaa tgcagtg atg tcg act    116
                                                   Met Ser Thr
                                                     1 ctt tgc cca ccg cca tct cca gct gtt gcc aag aca gag att gct tta    164
Leu Cys Pro Pro Pro Ser Pro Ala Val Ala Lys Thr Glu Ile Ala Leu
  5              10                  15 agt ggc aaa tca cct tta tta gca gct act ttt gct tac tgg gac aat    212
Ser Gly Lys Ser Pro Leu Leu Ala Ala Thr Phe Ala Tyr Trp Asp Asn
 20                  25                  30                  35 att ctt ggt cct aga gta agg cac att tgg gct cca aag aca gaa cag    260
Ile Leu Gly Pro Arg Val Arg His Ile Trp Ala Pro Lys Thr Glu Gln
             40                  45                  50 gta ctt ctc agt gat gga gaa ata act ttt ctt gcc aac cac act cta    308
Val Leu Leu Ser Asp Gly Glu Ile Thr Phe Leu Ala Asn His Thr Leu
     55                  60                  65 aat gga gaa atc ctt cga aat gca gag agt ggt gct ata gat gta aag    356
Asn Gly Glu Ile Leu Arg Asn Ala Glu Ser Gly Ala Ile Asp Val Lys
 70                  75                  80 ttt ttt gtc ttg tct gaa aag gga gtg att att gtt tca tta atc ttt    404
Phe Phe Val Leu Ser Glu Lys Gly Val Ile Ile Val Ser Leu Ile Phe
 85                  90                  95 gat gga aac tgg aat ggg gat cgc agc aca tat gga cta tca att ata    452
Asp Gly Asn Trp Asn Gly Asp Arg Ser Thr Tyr Gly Leu Ser Ile Ile
100                 105                 115 ctt cca cag aca gaa ctt agt ttc tac ctc cca ctt cat aga gtg tgt    500
Leu Pro Gln Thr Glu Leu Ser Phe Tyr Leu Pro Leu His Arg Val Cys
            120                 125                 130 gtt gat aga tta aca cat ata atc cgg aaa gga aga ata tgg atg cat    548
Val Asp Arg Leu Thr His Ile Ile Arg Lys Gly Arg Ile Trp Met His
            135                 140                 145 aag gaa aga caa gaa aat gtc cag aag att atc tta gaa ggc aca gag    596
Lys Glu Arg Gln Glu Asn Val Gln Lys Ile Ile Leu Glu Gly Thr Glu
            150                 155                 160 aga atg gaa gat cag ggt cag agt att att cca atg ctt act gga gaa    644
Arg Met Glu Asp Gln Gly Gln Ser Ile Ile Pro Met Leu Thr Gly Glu
165                 170                 175 gtg att cct gta atg gaa ctg ctt tca tct atg aaa tca cac agt gtt    692
Val Ile Pro Val Met Glu Leu Leu Ser Ser Met Lys Ser His Ser Val
180                 185                 190                 195 cct gaa gaa ata gat ata gct gat aca gta ctc aat gat gat gat att    740
Pro Glu Glu Ile Asp Ile Ala Asp Thr Val Leu Asn Asp Asp Asp Ile
                200                 205                 210 ggt gac agc tgt cat gaa ggc ttt ctt ctc aat gcc atc agc tca cac    788
Gly Asp Ser Cys His Glu Gly Phe Leu Leu Asn Ala Ile Ser Ser His
            215                 220                 225 ttg caa acc tgt ggc tgt tcc gtt gta gta ggt agc agt gca gag aaa    836
Leu Gln Thr Cys Gly Cys Ser Val Val Val Gly Ser Ser Ala Glu Lys
            230                 235                 240

| | | |
|---|---|---|
| gta aat aag ata gtc aga aca tta tgc ctt ttt ctg act cca gca gag<br>Val Asn Lys Ile Val Arg Thr Leu Cys Leu Phe Leu Thr Pro Ala Glu<br>245　　　　　　　　　250　　　　　　　　　255 | | 884 |
| aga aaa tgc tcc agg tta tgt gaa gca gaa tca tca ttt aaa tat gag<br>Arg Lys Cys Ser Arg Leu Cys Glu Ala Glu Ser Ser Phe Lys Tyr Glu<br>260　　　　　　　　　265　　　　　　　　　270　　　　　　　　275 | | 932 |
| tca ggg ctc ttt gta caa ggc ctg cta aag gat tca act gga agc ttt<br>Ser Gly Leu Phe Val Gln Gly Leu Leu Lys Asp Ser Thr Gly Ser Phe<br>　　　　　　　　　　280　　　　　　　　285　　　　　　　　　290 | | 980 |
| gtg ctg cct ttc cgg caa gtc atg tat gct cca tat ccc acc aca cac<br>Val Leu Pro Phe Arg Gln Val Met Tyr Ala Pro Tyr Pro Thr Thr His<br>295　　　　　　　　　300　　　　　　　　　305 | | 1028 |
| ata gat gtg gat gtc aat act gtg aag cag atg cca ccc tgt cat gaa<br>Ile Asp Val Asp Val Asn Thr Val Lys Gln Met Pro Pro Cys His Glu<br>310　　　　　　　　　315　　　　　　　　　320 | | 1076 |
| cat att tat aat cag cgt aga tac atg aga tcc gag ctg aca gcc ttc<br>His Ile Tyr Asn Gln Arg Arg Tyr Met Arg Ser Glu Leu Thr Ala Phe<br>325　　　　　　　　　330　　　　　　　　　335 | | 1124 |
| tgg aga gcc act tca gaa gaa gac atg gct cag gat acg atc atc tac<br>Trp Arg Ala Thr Ser Glu Glu Asp Met Ala Gln Asp Thr Ile Ile Tyr<br>340　　　　　　　　　345　　　　　　　　　350　　　　　　　　355 | | 1172 |
| act gac gaa agc ttt act cct gat ttg aat att ttt caa gat gtc tta<br>Thr Asp Glu Ser Phe Thr Pro Asp Leu Asn Ile Phe Gln Asp Val Leu<br>　　　　　　　　　　360　　　　　　　　365　　　　　　　　　370 | | 1220 |
| cac aga gac act cta gtg aaa gcc ttc ctg gat cag gtc ttt cag ctg<br>His Arg Asp Thr Leu Val Lys Ala Phe Leu Asp Gln Val Phe Gln Leu<br>375　　　　　　　　　380　　　　　　　　　385 | | 1268 |
| aaa cct ggc tta tct ctc aga agt act ttc ctt gca cag ttt cta ctt<br>Lys Pro Gly Leu Ser Leu Arg Ser Thr Phe Leu Ala Gln Phe Leu Leu<br>390　　　　　　　　　395　　　　　　　　　400 | | 1316 |
| gtc ctt cac aga aaa gcc ttg aca cta ata aaa tat ata gaa gac gat<br>Val Leu His Arg Lys Ala Leu Thr Leu Ile Lys Tyr Ile Glu Asp Asp<br>405　　　　　　　　　410　　　　　　　　　415 | | 1364 |
| acg cag aag gga aaa aag ccc ttt aaa tct ctt cgg aac ctg aag ata<br>Thr Gln Lys Gly Lys Lys Pro Phe Lys Ser Leu Arg Asn Leu Lys Ile<br>420　　　　　　　　　425　　　　　　　　　430　　　　　　　　435 | | 1412 |
| gac ctt gat tta aca gca gag ggc gat ctt aac ata ata atg gct ctg<br>Asp Leu Asp Leu Thr Ala Glu Gly Asp Leu Asn Ile Ile Met Ala Leu<br>　　　　　　　　　　440　　　　　　　　445　　　　　　　　　450 | | 1460 |
| gct gag aaa att aaa cca ggc tta cac tct ttt atc ttt gga aga cct<br>Ala Glu Lys Ile Lys Pro Gly Leu His Ser Phe Ile Phe Gly Arg Pro<br>455　　　　　　　　　460　　　　　　　　　465 | | 1508 |
| ttc tac act agt gtg caa gaa cga gat gtt cta atg act ttt taa<br>Phe Tyr Thr Ser Val Gln Glu Arg Asp Val Leu Met Thr Phe<br>470　　　　　　　　　475　　　　　　　　　480 | | 1553 |
| atgtgtaact taataagcct attccatcac aatcatgatc gctggtaaag tagctcagtg | | 1613 |
| gtgtggggaa acgttcccct ggatcatact ccagaattct gctctcagca attgcagtta | | 1673 |
| agtaagttac actacagttc tcacaagagc ctgtgagggg atgtcaggtg catcattaca | | 1733 |
| ttgggtgtct ctttttcctag atttatgctt ttgggataca gacctatgtt tacaatataa | | 1793 |
| taaatattat tgctatcttt taaagatata ataataggat gtaaacttga ccacaactac | | 1853 |
| tgttttttg aaatacatga ttcatggttt acatgtgtca aggtgaaatc tgagttggct | | 1913 |
| tttacagata gttgactttc tatcttttgg cattctttgg tgtgtagaat tactgtaata | | 1973 |
| cttctgcaat caactgaaaa ctagagcctt taaatgattt caattccaca gaaagaaagt | | 2033 |
| gagcttgaac ataggatgag ctttagaaag aaaattgatc aagcagatgt ttaattgaa | | 2093 |
| ttgattatta gatcctactt tgtggattta gtccctggga ttcagtctgt agaaatgtct | | 2153 |

```
aatagttctc tatagtccttt gttcctggtg aaccacagtt agggtgtttt gtttatttta    2213
ttgttcttgc tattgttgat attctatgta gttgagctct gtaaaaggaa attgtatttt    2273
atgttttagt aattgttgcc aacttttttaa attaattttc attattttg agccaaattg     2333 aaatgtgcac ctcctgtgcc ttttttctcc ttagaaaatc taattacttg gaacaagttc    2393
agatttcact ggtcagtcat tttcatcttg ttttcttctt gctaagtctt accatgtacc    2453
tgctttggca atcattgcaa ctctgagatt ataaaatgcc ttagagaata tactaactaa    2513
taagatcttt ttttcagaaa cagaaaatag ttccttgagt acttccttct gcatttctg     2573 cctatgtttt tgaagttgtt gctgtttgcc tgcaataggc tataaggaat agcaggagaa    2633
attttactga agtgctgttt tcctaggtgc tactttggca gagctaagtt atcttttgtt    2693
ttcttaatgc gtttggacca ttttgctggc tataaaataa ctgattaata taattctaac    2753
acaatgttga cattgtagtt acacaaacac aaataaatat tttatttaaa attctggaag    2813
taatataaaa gggaaaatat atttataaga aagggataaa ggtaatagag cccttctgcc    2873
ccccacccac caaatttaca caacaaaatg acatgttcga atgtgaaagg tcataatagc    2933
tttcccatca tgaatcagaa agatgtggac agcttgatgt tttagacaac cactgaacta    2993
gatgactgtt gtactgtagc tcagtcattt aaaaaatata taaatactac cttgtagtgt    3053
cccatactgt gttttttaca tggtagattc ttatttaagt gctaactggt tattttcttt    3113
ggctggttta ttgtactgtt atacagaatg taagttgtac agtgaaataa gttattaaag    3173
catgtgtaaa cattgttata tatcttttct cctaaatgga gaattttgaa taaaatatat    3233
ttgaaatttt g                                                         3244

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5
cacgaggctt tgatatttct tacaacgaat ttcatgtgta gacccactaa acagaagcta     60
taaaagttgc atggtcaaat aagtctgaga aagtctgcag atgatataat tcacctgaag    120
agtcacagta tgtagccaaa tgttaaaggt tttgagatgc catacagtaa atttaccaag    180
cattttctaa atttatttga ccacagaatc cctattttaa gcaacaactg ttacatccca    240
tggattccag gtgactaaag aatacttatt tcttaggata tgttttattg ataataacaa    300
ttaaaatttc agatatcttt cataagcaaa tcagtggtct ttttacttca tgttttaatg    360
ctaaaatatt ttcttttata gatagtcaga acattatgcc tttttctgac tccagcagag    420
agaaaatgct ccaggttatg tgaagcagaa tcatcattta aatatgagtc agggctcttt    480
gtacaaggcc tgctaaagga ttcaactgga agctttgtgc tgcctttccg gcaagtcatg    540
tatgctccat atcccaccac acacatagat gtggatgtca atactgtgaa gcagatgcca    600
ccctgtcatg aacatattta taatcagcgt agatacatga gatccgagct gacagccttc    660
tggagagcca cttcagaaga agacatggct cangatacga tcatctacac tgacgaaagc    720
```
tntactcctg atttgaatat ttttcaagat gtcttacaca g     761

<210> SEQ ID NO 6
<211> LENGTH: 1901
<212> TYPE: DNA
<213> ORGANISM: Homo sapiens
<220> FEATURE:
<221> NAME/KEY: CDS
<222> LOCATION: (125)..(793)

<400> SEQUENCE: 6
acgtaaccta cggtgtcccg ctaggaaaga gaggtgcgtc aaacagcgac aagttccgcc     60
cacgtaaaag atgacgcttg atatctccgg agcatttgga taatgtgaca gttggaatgc    120 agtg atg tcg act ctt tgc cca ccg cca tct cca gct gtt gcc aag aca    169
     Met Ser Thr Leu Cys Pro Pro Pro Ser Pro Ala Val Ala Lys Thr
     1               5                   10                  15 gag att gct tta agt ggc aaa tca cct tta tta gca gct act ttt gct    217
Glu Ile Ala Leu Ser Gly Lys Ser Pro Leu Leu Ala Ala Thr Phe Ala
                20                  25                  30 tac tgg gac aat att ctt ggt cct aga gta agg cac att tgg gct cca    265
Tyr Trp Asp Asn Ile Leu Gly Pro Arg Val Arg His Ile Trp Ala Pro
            35                  40                  45 aag aca gaa cag gta ctt ctc agt gat gga gaa ata act ttt ctt gcc    313
Lys Thr Glu Gln Val Leu Leu Ser Asp Gly Glu Ile Thr Phe Leu Ala
        50                  55                  60 aac cac act cta aat gga gaa atc ctt cga aat gca gag agt ggt gct    361
Asn His Thr Leu Asn Gly Glu Ile Leu Arg Asn Ala Glu Ser Gly Ala
    65                  70                  75 ata gat gta aag ttt ttt gtc ttg tct gaa aag gga gtg att att gtt    409
Ile Asp Val Lys Phe Phe Val Leu Ser Glu Lys Gly Val Ile Ile Val
80                  85                  90                  95 tca tta atc ttt gat gga aac tgg aat ggg gat cgc agc aca tat gga    457
Ser Leu Ile Phe Asp Gly Asn Trp Asn Gly Asp Arg Ser Thr Tyr Gly
                100                 105                 110 cta tca att ata ctt cca cag aca gaa ctt agt ttc tac ctc cca ctt    505
Leu Ser Ile Ile Leu Pro Gln Thr Glu Leu Ser Phe Tyr Leu Pro Leu
            115                 120                 125 cat aga gtg tgt gtt gat aga tta aca cat ata atc cgg aaa gga aga    553
His Arg Val Cys Val Asp Arg Leu Thr His Ile Ile Arg Lys Gly Arg
        130                 135                 140 ata tgg atg cat aag gaa aga caa gaa aat gtc cag aag att atc tta    601
Ile Trp Met His Lys Glu Arg Gln Glu Asn Val Gln Lys Ile Ile Leu
    145                 150                 155 gaa ggc aca gag aga atg gaa gat cag ggt cag agt att att cca atg    649
Glu Gly Thr Glu Arg Met Glu Asp Gln Gly Gln Ser Ile Ile Pro Met
160                 165                 170                 175 ctt act gga gaa gtg att cct gta atg gaa ctg ctt tca tct atg aaa    697
Leu Thr Gly Glu Val Ile Pro Val Met Glu Leu Leu Ser Ser Met Lys
                180                 185                 190 tca cac agt gtt cct gaa gaa ata gat ata gct gat aca gta ctc aat    745
Ser His Ser Val Pro Glu Glu Ile Asp Ile Ala Asp Thr Val Leu Asn
            195                 200                 205 gat gat gat att ggt gac agc tgt cat gaa ggc ttt ctt ctc aag taa    793
Asp Asp Asp Ile Gly Asp Ser Cys His Glu Gly Phe Leu Leu Lys
        210                 215                 220 gaattttct tttcataaaa gctggatgaa gcagatacca tcttatgctc acctatgaca    853
agatttggaa gaaagaaaat aacagactgt ctacttagat tgttctaggg acattacgta    913
tttgaactgt tgcttaaatt tgtgttattt ttcactcatt atatttctat atatatttgg    973

| | |
|---|---|
| tgttattcca tttgctattt aaagaaaccg agtttccatc ccagacaaga aatcatggcc | 1033 |
| ccttgcttga ttctggtttc ttgttttact tctcattaaa gctaacagaa tcctttcata | 1093 |
| ttaagttgta ctgtagatga acttaagtta tttaggcgta gaacaaaatt attcatattt | 1153 |
| atactgatct ttttccatcc agcagtggag tttagtactt aagagtttgt gcccttaaac | 1213 |
| cagactccct ggattaatgc tgtgtacccg tgggcaaggt gcctgaattc tctatacacc | 1273 |
| tatttcctca tctgtaaaat ggcaataata gtaatagtac ctaatgtgta gggttgttat | 1333 |
| aagcattgag taagataaat aatataaagc acttagaaca gtgcctggaa cataaaaaca | 1393 |
| cttaataata gctcatagct aacatttcct atttacattt cttctagaaa tagccagtat | 1453 |
| ttgttgagtg cctacatgtt agttcctta ctagttgctt tacatgtatt atcttatatt | 1513 |
| ctgtttaaa gtttcttcac agttacagat tttcatgaaa ttttacttt aataaaagag | 1573 |
| aagtaaaagt ataaagtatt cacttttatg ttcacagtct tttcctttag gctcatgatg | 1633 |
| gagtatcaga ggcatgagtg tgtttaacct aagagcctta atggcttgaa tcagaagcac | 1693 |
| tttagtcctg tatctgttca gtgtcagcct ttcatacatc attttaaatc ccatttgact | 1753 |
| ttaagtaagt cacttaatct ctctacatgt caatttcttc agctataaaa tgatggtatt | 1813 |
| tcaataaata aatacattaa ttaaatgata ttatactgac taattgggct gttttaaggc | 1873 |
| aaaaaaaaaa aaaaaaaaa aaaaaaaa | 1901 |

```
<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7
```

| | |
|---|---|
| agacgtaacc tacggtgtcc cgctaggaaa gagagatatc tccggagcat ttggataatg | 60 |
| tgacagttgg aatgcagtga tgtcgactct ttgcccaccg ccatctccag ctgttgccaa | 120 |
| gacagagatt gctttaagtg gcaaatcacc tttattagca gctacntttt gcttactggg | 180 |
| acaatattct tggtcctaga gtaaggcaca tttgggctcc aaagacagaa caggtacttc | 240 |
| tcagtgatgg agaaataact tttcttgcca accacactct aaatgaggaa atccttcgaa | 300 |
| atgcagagag tggtgctata gatgtaaagt ttttgtctt gtctgaaaag ggagtgatta | 360 |
| ttgtttcatt aatctttgat ggaaactgga atggggatcg cagcacatat ggactatcaa | 420 |
| ttatacttcc acagacagaa cttagtttct acctcccact tcatagagtg tgtgttgata | 480 |
| gattaacaca tataatccgg aaaggaagaa tatggatgca taggaaaga caagaaaatg | 540 |
| tccagaagat tatcttagaa gg | 562 |

```
<210> SEQ ID NO 8
<211> LENGTH: 798
<212> TYPE: DNA
<213> ORGANISM: Homo sapiens
<220> FEATURE:
<221> NAME/KEY: CDS
<222> LOCATION: (81)..(590)

<400> SEQUENCE: 8
```

| | |
|---|---|
| gggctctctt ttgggggcgg ggtctagcaa gagcagatat ctccggagca tttggataat | 60 |
| gtgacagttg gaatgcagtg atg tcg act ctt tgc cca ccg cca tct cca gct | 113 |
|                                   Met Ser Thr Leu Cys Pro Pro Pro Ser Pro Ala | |

```
                      1               5                    10
gtt gcc aag aca gag att gct tta agt ggc aaa tca cct tta tta gca       161
Val Ala Lys Thr Glu Ile Ala Leu Ser Gly Lys Ser Pro Leu Leu Ala
             15                  20                  25 gct act ttt gct tac tgg gac aat att ctt ggt cct aga gta agg cac       209
Ala Thr Phe Ala Tyr Trp Asp Asn Ile Leu Gly Pro Arg Val Arg His
         30                  35                  40 att tgg gct cca aag aca gaa cag gta ctt ctc agt gat gga gaa ata       257
Ile Trp Ala Pro Lys Thr Glu Gln Val Leu Leu Ser Asp Gly Glu Ile
     45                  50                  55 act ttt ctt gcc aac cac act cta aat gga gaa atc ctt cga aat gca       305
Thr Phe Leu Ala Asn His Thr Leu Asn Gly Glu Ile Leu Arg Asn Ala
 60                  65                  70                  75 gag agt ggt gct ata gat gta aag ttt ttt gtc ttg tct gaa aag gga       353
Glu Ser Gly Ala Ile Asp Val Lys Phe Phe Val Leu Ser Glu Lys Gly
                 80                  85                  90 gtg att att gtt tca tta atc ttt gat gga aac tgg aat ggg gat cgc       401
Val Ile Ile Val Ser Leu Ile Phe Asp Gly Asn Trp Asn Gly Asp Arg
             95                 100                 105 agc aca tat gga cta tca att ata ctt cca cag aca gaa ctt agt ttc       449
Ser Thr Tyr Gly Leu Ser Ile Ile Leu Pro Gln Thr Glu Leu Ser Phe
         110                 115                 120 tac ctc cca ctt cat aga gtg tgt gtt gat aga tta aca cat ata atc       497
Tyr Leu Pro Leu His Arg Val Cys Val Asp Arg Leu Thr His Ile Ile
     125                 130                 135 cgg aaa gga aga ata tgg atg cat aag gaa aga caa gaa aat gtc cag       545
Arg Lys Gly Arg Ile Trp Met His Lys Glu Arg Gln Glu Asn Val Gln
140                 145                 150                 155 aag att atc tta gaa ggc aca gag aga atg gaa gat cag ggt cag           590
Lys Ile Ile Leu Glu Gly Thr Glu Arg Met Glu Asp Gln Gly Gln
                 160                 165                 170 agtattattc caatgcttac tggagaagtg attcctgtaa tgggactgct ttcatctatg     650
aaatcacaca gtgttcctga agaaatagat atagctgata cagtactcca tgatgatgat     710
atttggtgac agctgtcatg aaaggctttc ttctcaagta ggatttttt cttttcataa      770 aagctgggat gaagccagat tcccatct                                        798

<210> SEQ ID NO 9
<211> LENGTH: 169
<212> TYPE: DNA
<213> ORGANISM: Homo sapiens

<400> SEQUENCE: 9
aaacagcgac aagttccgcc cacgtaaaag atgatgcttg gtgtgtcagc cgtccctgct      60
gcccggttgc ttctcttttg ggggcgggt ctagcaagag cagatatctc cggagcattt     120
ggataatgtg acagttggaa tgcggtgatg tcgactcttt gcccaccgc                 169

<210> SEQ ID NO 10
<211> LENGTH: 176
<212> TYPE: DNA
<213> ORGANISM: Homo sapiens

<400> SEQUENCE: 10
aaaacgtcat cgcacataga aaacagacag acgtaaccta cggtgtcccg ctaggaaaga     60
gaggtgcgtc aaacagcgac aagttccgcc cacgtaaaag atgacgcttg atatctccgg    120
agcatttgga taatgtgaca gttggaatgc agtgatgtcg actctttgcc caccgc        176
```

```
<210> SEQ ID NO 11
<211> LENGTH: 783
<212> TYPE: DNA
<213> ORGANISM: homo sapiens

<400> SEQUENCE: 11
gcctctcagt acccgaggct ccctttctc gagcccgcag cggcagcgct cccagcgggt    60
ccccgggaag gagacagctc gggtactgag ggcgggaaag caaggaagag gccagatccc   120
catcccttgt ccctgcgccg ccgccgccgc cgccgccgcc gggaagcccg ggcccggat    180 gcaggcaatt ccaccagtcg ctagaggcga agcccgaca cccagcttcg gtcagagaaa    240
tgagagggaa agtaaaaatg cgtcgagctc tgaggagagc ccccgcttct acccgcgcct   300
cttcccggca gccgaacccc aaacagccac ccgccaggat gccgcctcct cactcaccca   360
ctcgccaccg cctgcgcctc cgccgccgcg ggcgcaggca ccgcaaccgc agccccgccc   420
cgggcccgcc cccgggcccg ccccgaccac gccccggccc cggccccggc cccggccccg   480
gcccctagcg cgcgactcct gagttccaga gcttgctaca ggctgcggtt gtttccctcc   540
ttgttttctt ctggttaatc tttatcaggt cttttcttgt tcaccctcag cgagtactgt   600
gagagcaagt agtggggaga gagggtggga aaaacaaaaa cacacacctc ctaaacccac   660
acctgctctt gctagacccc gccccaaaa gagaagcaac cgggcagcag ggacggctga    720
cacaccaagc gtcatctttt acgtgggcgg aacttgtcgc tgtttgacgc acctctcttt    780
cct                                                                  783

<210> SEQ ID NO 12
<211> LENGTH: 45
<212> TYPE: DNA
<213> ORGANISM: Artificial sequence
<220> FEATURE:
<223> OTHER INFORMATION: Primer

<400> SEQUENCE: 12
cgactggagc acgaggacac tgaaaagatg acgcttggtg tgtca                    45

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
cccacacctg ctcttgctag a                                              21

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
cgactggagc acgaggacac tg                                             22

<210> SEQ ID NO 15
<211> LENGTH: 23
<212> TYPE: DNA
<213> ORGANISM: Artificial sequence
<220> FEATURE:
<223> OTHER INFORMATION: Probe
```

```
<400> SEQUENCE: 15
cccaaaagag aagcaaccgg gca                                          23

<210> SEQ ID NO 16
<211> LENGTH: 38
<212> TYPE: DNA
<213> ORGANISM: Artificial sequence
<220> FEATURE:
<223> OTHER INFORMATION: Primer

<400> SEQUENCE: 16
cgactggagc acgaggacac tgacggctgc cgggaaga                          38

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
agaaatgaga gggaaagtaa aaatgc                                       26

<210> SEQ ID NO 18
<211> LENGTH: 22
<212> TYPE: DNA
<213> ORGANISM: Artificial sequence
<220> FEATURE:
<223> OTHER INFORMATION: Primer

<400> SEQUENCE: 18
cgactggagc acgaggacac tg                                           22

<210> SEQ ID NO 19
<211> LENGTH: 23
<212> TYPE: DNA
<213> ORGANISM: Artificial sequence
<220> FEATURE:
<223> OTHER INFORMATION: Probe

<400> SEQUENCE: 19
aggagagccc ccgcttctac ccg                                          23

<210> SEQ ID NO 20
<211> LENGTH: 42
<212> TYPE: DNA
<213> ORGANISM: Artificial sequence
<220> FEATURE:
<223> OTHER INFORMATION: Primer

<400> SEQUENCE: 20
cgactggagc acgaggacac tgacgctgag ggtgaacaag aa                     42

<210> SEQ ID NO 21
<211> LENGTH: 21
<212> TYPE: DNA
<213> ORGANISM: Artificial sequence
<220> FEATURE:
<223> OTHER INFORMATION: Primer

<400> SEQUENCE: 21
gagttccaga gcttgctaca g                                            21

<210> SEQ ID NO 22
<211> LENGTH: 22
```

```
<212> TYPE: DNA
<213> ORGANISM: Artificial sequence
<220> FEATURE:
<223> OTHER INFORMATION: Primer

<400> SEQUENCE: 22
cgactggagc acgaggacac tg                                            22

<210> SEQ ID NO 23
<211> LENGTH: 24
<212> TYPE: DNA
<213> ORGANISM: Artificial sequence
<220> FEATURE:
<223> OTHER INFORMATION: Probe

<400> SEQUENCE: 23
ctgcggttgt ttccctcctt gttt                                          24

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
ggcaaattca acggcacagt                                               20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
gggtctcgct cctggaagat                                               20

<210> SEQ ID NO 26
<211> LENGTH: 27
<212> TYPE: DNA
<213> ORGANISM: Artificial sequence
<220> FEATURE:
<223> OTHER INFORMATION: Probe

<400> SEQUENCE: 26
aaggccgaga atgggaagct tgtcatc                                       27

<210> SEQ ID NO 27
<211> LENGTH: 43
<212> TYPE: DNA
<213> ORGANISM: Artificial sequence
<220> FEATURE:
<223> OTHER INFORMATION: Primer

<400> SEQUENCE: 27
tagtcctgca ggtttaaacg aattcgtgag tgaggaggcg gca                     43

<210> SEQ ID NO 28
<211> LENGTH: 37
<212> TYPE: DNA
<213> ORGANISM: Artificial sequence
<220> FEATURE:
<223> OTHER INFORMATION: Primer

<400> SEQUENCE: 28
```
agcagagctc agattacgta cccttgttgt gaacaac    37

<210> SEQ ID NO 29
<211> LENGTH: 33
<212> TYPE: DNA
<213> ORGANISM: Artificial sequence
<220> FEATURE:
<223> OTHER INFORMATION: Primer

<400> SEQUENCE: 29
caatgtcaac gtctggcatt acttctactt ttg    33

<210> SEQ ID NO 30
<211> LENGTH: 43
<212> TYPE: DNA
<213> ORGANISM: Artificial sequence
<220> FEATURE:
<223> OTHER INFORMATION: Primer

<400> SEQUENCE: 30
tagggcgaat tgaatttagc ggccgcactg gcaggatcat agc    43

<210> SEQ ID NO 31
<211> LENGTH: 30
<212> TYPE: DNA
<213> ORGANISM: Artificial sequence
<220> FEATURE:
<223> OTHER INFORMATION: Primer

<400> SEQUENCE: 31
tacgtaatct gagctctgct tatatagacc    30

<210> SEQ ID NO 32
<211> LENGTH: 42
<212> TYPE: DNA
<213> ORGANISM: Artificial sequence
<220> FEATURE:
<223> OTHER INFORMATION: Primer

<400> SEQUENCE: 32
aatgccagac gttgacattg attattgact agttattaat ag    42

<210> SEQ ID NO 33
<211> LENGTH: 23
<212> TYPE: DNA
<213> ORGANISM: Artificial sequence
<220> FEATURE:
<223> OTHER INFORMATION: Primer

<400> SEQUENCE: 33
gttaggctct gggagagtag ttg    23

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
cctggagcag gtaaatgctg g    21

<210> SEQ ID NO 35

<400> SEQUENCE: 35

000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tagtgcggac ctacccacga                                           20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ggggccgggg ccggggccgg                                           20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
gggccggggc cggggccggg                                           20

<210> SEQ ID NO 44
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 44
ggccggggcc ggggccgggg                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gccggggccg gggccggggc                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ccggggccgg ggccggggcc                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cggggccggg gccggggccg                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
aggaaagaga ggtgcgtcaa                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
aaagagaggt gcgtcaaaca                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gagaggtgcg tcaaacagcg                                              20
```

```
<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
aggtgcgtca aacagcgaca                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tgcgtcaaac agcgacaagt                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
gtcaaacagc gacaagttcc                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
aaacagcgac aagttccgcc                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
cagcgacaag ttccgcccac                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
cgacaagttc cgcccacgta                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 57
caagttccgc ccacgtaaaa                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
gttccgccca cgtaaaagat                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ccgcccacgt aaaagatgac                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
cccacgtaaa agatgacgct                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
acgtaaaaga tgacgcttgg                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
taaaagatga cgcttggtgt                                               20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
aagatgacgc ttggtgtgtc                                               20

<210> SEQ ID NO 64
<211> LENGTH: 20
```

-continued

```
<212> TYPE: DNA
<213> ORGANISM: Artificial sequence
<220> FEATURE:
<223> OTHER INFORMATION: Synthetic oligonucleotide

<400> SEQUENCE: 64
atgacgcttg gtgtgtcagc                                              20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
acgcttggtg tgtcagccgt                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
cttggtgtgt cagccgtccc                                              20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
tcagccgtcc ctgctgcccg                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gccgtccctg ctgcccggtt                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gtccctgctg cccggttgct                                              20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
```

| cctgctgccc ggttgcttct | 20 |

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71

| gctgcccggt tgcttctctt | 20 |

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72

| gcccggttgc ttctcttttg | 20 |

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73

| ctagcaagag caggtgtggg | 20 |

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74

| gcaggtgtgg gtttaggagg | 20 |

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75

| ggtgtgggtt taggaggtgt | 20 |

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76

| gctctcacag tactcgctga | 20 |

<210> SEQ ID NO 77
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 77
acagtactcg ctgagggtga                                               20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
taaagattaa ccagaagaaa                                               20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
ccgcagcctg tagcaagctc                                               20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
actcaggagt cgcgcgctag                                               20

<210> SEQ ID NO 81
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 81
gacaagggta cgtaatctgt c                                             21

<210> SEQ ID NO 82
<211> LENGTH: 99
<212> TYPE: DNA
<213> ORGANISM: Artificial sequence
<220> FEATURE:
<223> OTHER INFORMATION: Synthetic oligonucleotide

<400> SEQUENCE: 82
gacaagggta cgtaatctgt ctagagctag aaatagcaag ttaaataag gctagtccgt    60 tatcaacttg aaaaagtggc accgagtcgg tgcttttttt                         99

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
```

```
ggggccgggg ccggcg                                                   16

<210> SEQ ID NO 84
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 84
cagcagcagc agcagcagc                                                19
```

COMPOSITIONS FOR MODULATING EXPRESSION OF C9ORF72 ANTISENSE TRANSCRIPT

SEQUENCE LISTING

The present application is being filed along with a Sequence Listing in electronic format. The Sequence Listing is provided as a file entitled BIOL0261USASEQ_ST25.txt created Oct. 10, 2017, which is 84 Kb in size. The information in the electronic format of the sequence listing is incorporated herein by reference in its entirety.

FIELD

Provided are compositions and methods for modulating expression of C9ORF72 antisense transcript in an animal. Such compositions and methods are useful to treat, prevent, ameliorate, or slow progression of neurodegenerative diseases, including amyotrophic lateral sclerosis (ALS), frontotemporal dementia (FTD), corticobasal degeneration syndrome (CBD), atypical Parkinsonian syndrome, and olivopontocerebellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). This mutation has been found to be the most common genetic cause of ALS and FTD. It is postulated that the ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

There are currently no effective therapies to treat such neurodegenerative diseases. Therefore, it is an object to provide compositions and methods for the treatment of such neurodegenerative diseases.

SUMMARY

Provided herein are compositions and methods for modulating expression and levels of C9ORF72 antisense transcript in cells, tissues, and animals. In certain embodiments, C9ORF72 antisense transcript specific inhibitors modulate expression of C9ORF72 antisense transcript. In certain embodiments, C9ORF72 antisense transcript specific inhibitors are nucleic acids, proteins, or small molecules. In certain embodiments, C9ORF72 antisense transcript specific inhibitors are antisense compounds. In certain embodiments, C9ORF72 antisense compounds are modified oligonucleotides. In certain embodiments, the modified oligonucleotides are single-stranded.

In certain embodiments, modulation can occur in a cell or tissue. In certain embodiments, the cell or tissue is in an animal. In certain embodiments, the animal is a human. In certain embodiments, C9ORF72 antisense transcript levels are reduced. In certain embodiments, C9ORF72 antisense transcript associated RAN translation products are reduced. In certain embodiments, the C9ORF72 antisense transcript associated RAN translation products are poly-(proline-alanine), poly-(proline-arginine), and poly-(proline-glycine). In certain embodiments, the C9ORF72 antisense transcript contains a hexanucleotide repeat expansion. In certain embodiments, the hexanucleotide repeat is transcribed in the antisense direction from the C9ORF72 gene. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGCCCC, CCCCCC, GCCCCC, and/or CGCCCC repeats. In certain embodiments, the hexanucleotide repeat expansion comprises more than 30 GGCCCC, CCCCCC, GCCCCC, and/or CGCCCC repeats. In certain embodiments, the hexanucleotide repeat expansion comprises more than 100 GGCCCC, CCCCCC, GCCCCC, and/or CGCCCC repeats. In certain embodiments, the hexanucleotide repeat expansion comprises more than 500 GGCCCC, CCCCCC, GCCCCC, and/or CGCCCC repeats. In certain embodiments, the hexanucleotide repeat expansion comprises at least 1000 GGCCCC, CCCCCC, GCCCCC, and/or CGCCCC repeats. In certain embodiments, the hexanucleotide repeat expansion is associated with nuclear foci. In certain embodiments, C9ORF72 antisense transcript associated RAN translation products are associated with nuclear foci. In certain embodiments, the antisense transcript associated RAN translation products are poly-(proline-alanine) and/or poly-(proline-arginine). In certain embodiments, the compositions and methods described herein are useful for reducing C9ORF72 antisense transcript levels, C9ORF72 antisense transcript associated RAN translation products, and nuclear foci. Such reduction can occur in a time-dependent manner or in a dose-dependent manner.

Also provided are methods useful for preventing, treating, ameliorating, and slowing progression of diseases and conditions associated with C9ORF72. In certain embodiments, such diseases and conditions associated with C9ORF72 are neurodegenerative diseases. In certain embodiments, the neurodegenerative disease is amyotrophic lateral sclerosis (ALS), frontotemporal dementia (FTD), corticobasal degeneration syndrome (CBD), atypical Parkinsonian syndrome, or olivopontocerebellar degeneration (OPCD).

Such diseases and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 antisense transcript specific inhibitor to an individual in need thereof. In certain embodiments, the C9ORF72 antisense transcript specific inhibitor is a nucleic acid. In certain embodiments, the nucleic acid is an antisense compound. In certain embodiments, the antisense compound is a modified oligonucleotide. In certain embodiments, the antisense oligonucleotide is complementary to a C9ORF72 antisense transcript.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein product encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 antisense transcript" means transcripts produced from the non-coding strand (also antisense strand and template strand) of the C9ORF72 gene. The C9ORF72 antisense transcript differs from the canonically transcribed "C9ORF72 sense transcript", which is produced from the coding strand (also sense strand) of the C9ORF72 gene.

"C9ORF72 antisense transcript associated RAN translation products" means aberrant peptide or di-peptide polymers translated through RAN translation (i.e., repeat-associated, and non-ATG-dependent translation). In certain embodiments, the C9ORF72 antisense transcript associated RAN translation products are any of poly-(proline-alanine), poly-(proline-arginine), and poly-(proline-glycine).

"C9ORF72 antisense transcript specific inhibitor" refers to any agent capable of specifically inhibiting the expression of C9ORF72 antisense transcript and/or its expression products at the molecular level. For example, C9ORF72 specific antisense transcript inhibitors include nucleic acids (including antisense compounds), siRNAs, aptamers, antibodies, peptides, small molecules, and other agents capable of inhibiting the expression of C9ORF72 antisense transcript and/or its expression products, such as C9ORF72 antisense transcript associated RAN translation products.

"C9ORF72 associated disease" means any disease associated with any C9ORF72 nucleic acid or expression product thereof, regardless of which DNA strand the C9ORF72 nucleic acid or expression product thereof is derived from. Such diseases may include a neurodegenerative disease. Such neurodegenerative diseases may include ALS and FTD.

"C9ORF72 foci" means nuclear foci comprising a C9ORF72 transcript. In certain embodiments, a C9ORF72 foci comprises at least one C9ORF72 sense transcript (herein "C9ORF72 sense foci"). In certain embodiments, C9ORF72 sense foci comprise C9ORF72 sense transcripts comprising any of the following hexanucleotide repeats: GGGGCC, GGGGGG, GGGGGC, and/or GGGGCG. In certain embodiments, a C9ORF72 foci comprises at least one C9ORF72 antisense transcript (herein "C9ORF72 antisense foci"). In certain embodiments, C9ORF72 antisense foci comprise C9ORF72 antisense transcripts comprising any of the following hexanucleotide repeats: GGCCCC, CCCCCC, GCCCCC, and/or CGCCCC. In certain embodiments, C9ORF72 foci comprise both C9ORF72 sense transcripts and C9ORF72 antisense transcripts.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise any of the following hexanucleotide repeats: GGGGCC, GGGGGG, GGGGGC, GGGGCG, GGCCCC, CCCCCC, GCCCCC, and/or CGCCCC. In certain embodiments, the hexanucleotide repeat is repeated at least 30 times, more than 30 times, more than 100 times, more than 500 times, or more than 1000 times. Such diseases may include a neurodegenerative disease. Such neurodegenerative diseases may include ALS and FTD.

"C9ORF72 nucleic acid" means any nucleic acid derived from the C9ORF72 locus, regardless of which DNA strand the C9ORF72 nucleic acid is derived from. In certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein. In certain embodiments, a C9ORF72 nucleic acid includes transcripts produced from the coding strand of the C9ORF72 gene. C9ORF72 sense transcripts are examples of C9ORF72 nucleic acids. In certain embodiments, a C9ORF72 nucleic acid includes transcripts produced from the non-coding strand of the C9ORF72 gene. C9ORF72 antisense transcripts are examples of C9ORF72 nucleic acids.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 transcript" means a RNA transcribed from C9ORF72. In certain embodiments, a C9ORF72 transcript is a C9ORF72 sense transcript. In certain embodiments, a C9ORF72 transcript is a C9ORF72 antisense transcript.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information, regardless of which DNA strand the coded information is derived from, is converted into structures present and operating in a cell. Such structures include, but are not limited to the products of transcription and translation, including RAN translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Hexanucleotide repeat expansion" means a series of six bases (for example, GGGGCC, GGGGGG, GGGGGC, GGGGCG, GGCCCC, CCCCCC, GCCCCC, and/or CGCCCC) repeated at least twice. In certain embodiments, the hexanucleotide repeat expansion may be located in intron 1 of a C9ORF72 nucleic acid. In certain embodiments, the hexanucleotide repeat may be transcribed in the antisense direction from the C9ORF72 gene. In certain embodiments, a pathogenic hexanucleotide repeat expansion includes more than 30, more than 100, more than 500, or more than 1000 repeats of GGGGCC, GGGGGG, GGGGGC, GGGGCG, GGCCCC, CCCCCC, GCCCCC, and/or CGCCCC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 30 or fewer repeats of GGGGCC, GGGGGG, GGGGGC, GGGGCG, GGCCCC, CCCCCC, GCCCCC, and/or CGCCCC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. In certain embodiments, the C9ORF72 associated disease is a C9ORF72 hexanucleotide repeat expansion associated disease. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting expression of a C9ORF72 antisense transcript" means reducing the level or expression of a C9ORF72 antisense transcript and/or its expression products (e.g., RAN translation products). In certain embodiments, C9ORF72 antisense transcripts are inhibited in the presence of an antisense compound targeting a C9ORF72 antisense transcript, including an antisense oligonucleotide targeting a C9ORF72 antisense transcript, as compared to expression of C9ORF72 antisense transcript levels in the absence of a C9ORF72 antisense compound, such as an antisense oligonucleotide.

"Inhibiting expression of a C9ORF72 sense transcript" means reducing the level or expression of a C9ORF72 sense transcript and/or its expression products (e.g., a C9ORF72 mRNA and/or protein). In certain embodiments, C9ORF72 sense transcripts are inhibited in the presence of an antisense compound targeting a C9ORF72 sense transcript, including an antisense oligonucleotide targeting a C9ORF72 sense transcript, as compared to expression of C9ORF72 sense transcript levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar.

Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

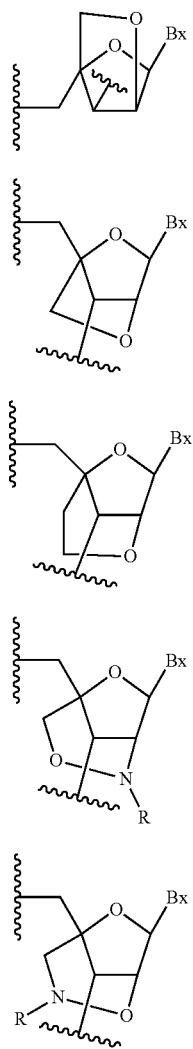

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. In certain embodiments, an antisense oligonucleotide targeted to C9ORF72sense transcript is a pharmaceutical agent. In certain embodiments, an antisense oligonucleotide targeted to C9ORF72antisense transcript is a pharmaceutical agent.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods, compounds, and compositions for modulating expression and levels of C9ORF72 antisense transcript. Certain embodiments provide methods, compounds, and compositions for inhibiting expression and levels of C9ORF72 antisense transcript.

Certain embodiments provide antisense compounds targeted to a C9ORF72 antisense transcript. In certain embodiments, the C9ORF72 antisense transcript is the sequence set forth in SEQ ID NO: 11, which is a sequence that is complementary to nucleotides 1159 to 1929 of SEQ ID NO: 2 (the complement of GENBANK Accession No. NT_008413.18 truncated from nucleotides 27535000 to 27565000).

Certain embodiments provide methods, compounds, and compositions for the treatment, prevention, amelioration, or slowing progression of disease associated with C9ORF72 antisense transcript in an individual in need thereof. Also contemplated are methods for the preparation of a medicament for the treatment, prevention, amelioration, or slowing progression of a disease associated with C9ORF72 antisense transcript. C9ORF72 antisense transcript diseases include amyotrophic lateral sclerosis (ALS), frontotemporal dementia (FTD), corticobasal degeneration syndrome (CBD), atypical Parkinsonian syndrome, or olivopontocerebellar degeneration (OPCD).

The present disclosure provides the following non-limiting numbered embodiments:

Embodiment 1. A compound comprising a modified oligonucleotide consisting of 12-30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobases sequences of SEQ ID NOs 42-80.

Embodiment 2. The compound of embodiment 1, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

Embodiment 3. The compound of embodiment 2, wherein the C9ORF72 antisense transcript has the nucleobase sequence of SEQ ID NO: 11.

Embodiment 4. The compound of any of embodiments 1-3, wherein the modified oligonucleotide is a single-stranded modified oligonucleotide.

Embodiment 5. The compound of any of embodiments 1-4, wherein the modified oligonucleotide comprises at least one modified internucleoside linkage.

Embodiment 6. The compound of any of embodiment 5, wherein the at least one modified internucleoside linkage is a phosphorothioate internucleoside linkage.

Embodiment 7. The compound of embodiments 5 or 6, wherein the modified oligonucleotide comprises at least one phosphodiester linkage.

Embodiment 8. The compound of embodiment 6, wherein each internucleoside linkage is a phosphorothioate internucleoside linkage.

Embodiment 9. The compound of any of embodiments 1-8, wherein at least one nucleoside of the modified oligonucleotide comprises a modified nucleobase.

Embodiment 10. The compound of embodiment 9, wherein the modified nucleobase is a 5-methylcytosine.

Embodiment 11. The compound of any of embodiments 1-10, wherein at least one nucleoside of the modified oligonucleotide comprises a modified sugar.

Embodiment 12. The compound of embodiment 11, wherein each nucleoside of the modified oligonucleotide comprises a modified sugar.

Embodiment 13. The compound of embodiments 11 or 12, wherein the modified sugar is a bicyclic sugar.

Embodiment 14. The compound of embodiment 13, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently selected from H, C$_1$-C$_6$ alkyl, and C$_1$-C$_6$ alkoxy.

Embodiment 15. The compound of embodiment 14, wherein the chemical bridge is 4'-CH(R)—O-2' and wherein R is methyl.

Embodiment 16. The compound of embodiment 14, wherein the chemical bridge is 4'-CH(R)—O-2' and wherein R is H.

Embodiment 17. The compound of embodiment 14, wherein the chemical bridge is 4'-CH(R)—O-2' and wherein R is —CH$_2$—O—CH$_3$.

Embodiment 18. The compound of embodiments 11 or 12, wherein the modified sugar comprises a 2'-O-methoxyethyl group.

Embodiment 19. The compound of any of embodiments 1-11 and 13-18, wherein the modified oligonucleotide is a gapmer.

Embodiment 20. The compound of embodiment 19, wherein the gapmer is a 5-10-5 MOE gapmer.

Embodiment 21. A composition comprising the compound of any preceding embodiment or salt thereof and at least one of a pharmaceutically acceptable carrier or diluent.

Embodiment 22. The composition of embodiment 21 further comprising a C9ORF72 sense transcript specific inhibitor.

Embodiment 23. The composition of embodiment 22, wherein the C9ORF72 sense transcript specific inhibitor is any of a nucleic acid, aptamer, antibody, peptide, or small molecule.

Embodiment 24. The composition of embodiment 23, wherein the nucleic acid is a single-stranded nucleic acid or a double-stranded nucleic acid.

Embodiment 25. The composition of embodiment 23, wherein the nucleic acid is a siRNA.

Embodiment 26. The composition of embodiment 22, wherein the C9ORF72 sense transcript inhibitor is an antisense compound.

Embodiment 27. The composition of embodiment 26, wherein the antisense compound is an antisense oligonucleotide.

Embodiment 28. The composition of embodiment 26, wherein the antisense compound is a modified oligonucleotide.

Embodiment 29. The composition of embodiment 28, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 sense transcript.

Embodiment 30. The compound of embodiment 29, wherein the C9ORF72 sense transcript has the nucleobase sequence of SEQ ID NO: 1-10.

Embodiment 31. Use of the compound or composition of any preceding embodiment for the manufacture of a medicament for treating a neurodegenerative disease.

Embodiment 32. A method comprising administering to an animal the compound or composition of any preceding embodiment.

Embodiment 33. The method of embodiment 32, wherein the animal is a human.

Embodiment 34. The method of embodiments 32 or 33, wherein the compound prevents, treats, ameliorates, or slows progression of at least one symptom of a C9ORF72 associated disease.

Embodiment 35. The method of embodiment 34, wherein the at least one symptom is selected from among impaired motor function, difficulty with respiration, muscle weakness, fasciculation and cramping of muscles, difficulty in projecting the voice, shortness of breath, difficulty in breathing and swallowing, inappropriate social behavior, lack of empathy, distractibility, changes in food preference, agitation, blunted emotions, neglect of personal hygiene, repetitive or compulsive behavior, and decreased energy and motivation.

Embodiment 36. The method of embodiment 34, wherein the C9ORF72 associated disease is amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 37. The method of embodiment 36, wherein the amyotrophic lateral sclerosis (ALS) is familial ALS.

Embodiment 38. The method of embodiment 36, wherein the amyotrophic lateral sclerosis (ALS) is sporadic ALS.

Embodiment 39. The method of any of embodiments 32-38, wherein the administering reduces C9ORF72 antisense transcript associated RAN translation products.

Embodiment 40. The method of embodiment 39, wherein the C9ORF72 antisense transcript associated RAN translation products are any of poly-(proline-alanine), poly-(proline-arginine), and poly-(proline-glycine).

Embodiment 41. The method of any of embodiments 32-40, wherein the administering is parenteral administration.

Embodiment 42. The method of embodiment 41, wherein the parenteral administration is any of injection or infusion.

Embodiment 43. The method of embodiment 42, wherein the parenteral administration is directly into the central nervous system (CNS).

Embodiment 44. The method of embodiments 41 or 42, wherein the parenteral administration is any of intrathecal administration or intracerebroventricular administration.

Embodiment 45. The method of any of embodiments 32-44, wherein the administering reduces C9ORF72 antisense foci.

Embodiment 46. The method of any of embodiments 32-44, wherein the administering reduces C9ORF72 sense foci.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$—O-2' bridge, wherein n is 1 or 2; and 4'-CH$_2$—O—CH$_2$-2'. In certain embodiments, the bicyclic sugar is comprises a 4'-CH(CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

Nucleotide sequences that encode the C9ORF72 antisense transcript include, without limitation, the following: SEQ ID NO: 11 is a sequence that is complementary to nucleotides 1159 to 1929 of SEQ ID NO: 2 (the complement of GENBANK Accession No. NT_008413.18 truncated from nucleotides 27535000 to 27565000).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_1$)—(CH$_2$)$_2$—N(R$_m$)(R$_n$), where each R$_1$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618;

US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from $-[C(R_a)(R_b)]_n-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, $-[C(R_a)(R_b)]_n-$, $-[C(R_a)(R_b)]_n-O-$, $-C(R_aR_b)-N(R)-O-$ or $-C(R_aR_b)-O-N(R)-$. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

In certain embodiment, bicyclic nucleosides have the formula:

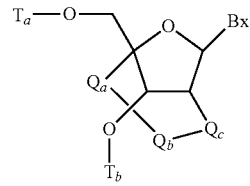

wherein:
Bx is a heterocyclic base moiety;
-$Q_a$-$Q_b$-$Q_c$- is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

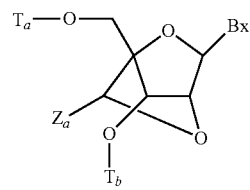

wherein:
Bx is a heterocyclic base moiety;
$T_a$ and $T_b$ are each, independently, H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

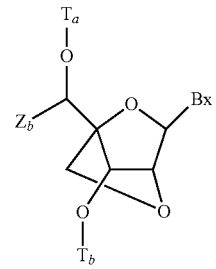

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

[Structure with $T_a$—O, $q_a$, $q_b$, Bx, $O$—$T_b$, $q_c$, $q_d$, N, $OR_d$]

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

[Structure with $T_a$—O, $q_a$, $q_b$, Bx, $O$—$T_b$, $q_e$, $q_f$, O]

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

[Structure with $T_a$—O, Bx, $O$—$T_b$, $q_i$, $q_j$, $q_k$, $q_l$]

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2') BNA (B) β-D-methyleneoxy (4'-$CH_2$—O-2') BNA (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy) (4'-CH($CH_3$)—O-2') BNA (also referred to as constrained ethyl or cEt), (G) methylenethio (4'-$CH_2$—S-2') BNA, (H) methylene-amino (4'-$CH_2$—

N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

(A)
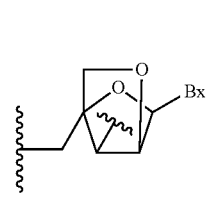

(B)
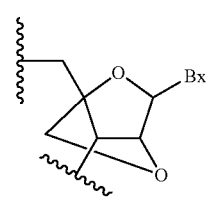

(C)
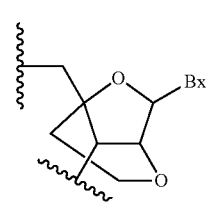

(D)
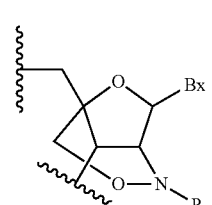

(E)
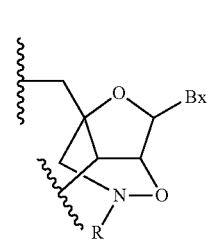

(F)
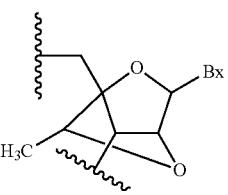

(G)
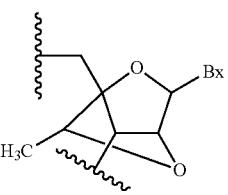

(H)
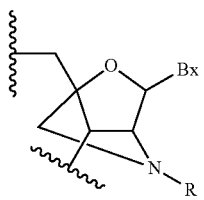

(I)
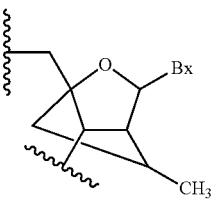

(J)
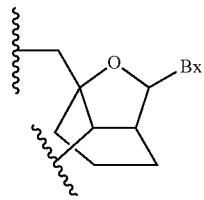

(K)
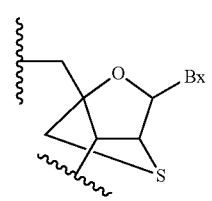

wherein Bx is the base moiety and R is, independently, H, a protecting group, C$_1$-C$_6$ alkyl or C$_1$-C$_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

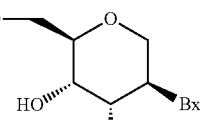
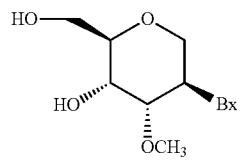
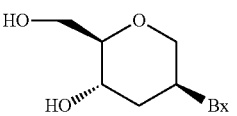

In certain embodiment, sugar surrogates are selected having the formula:

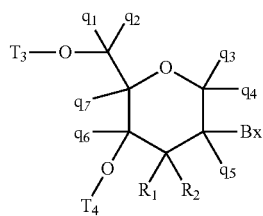

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

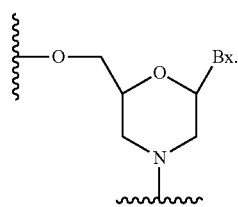

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

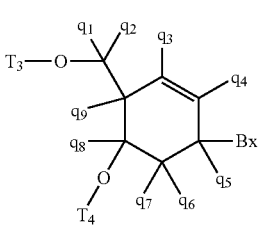

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. Bioorg. & Med. Chem., 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118, 800; 5,319,080; 5,359,044; 5,393,878; 5,446,137; 5,466, 786; 5,514,785; 5,519,134; 5,567,811; 5,576,427; 5,591, 722; 5,597,909; 5,610,300; 5,627,053; 5,639,873; 5,646, 265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Strand Specific Semi-Quantitative PCR Analysis of Target RNA Levels

Analysis of specific, low abundance target RNA strand levels may be accomplished by reverse transcription, PCR, and gel densitometry analysis using the Gel Logic 200 Imaging System and Kodak MI software (Kodak Scientific Imaging Systems, Rochester, N.Y., USA) according to manufacturer's instructions.

RT-PCR reactions are carried out as taught in Ladd, P. D., et al, (Human Molecular Genetics, 2007, 16, 3174-3187) and in Sopher, B. L., et al, (Neuron, 2011, 70, 1071-1084) and such methods are well known in the art.

The PCR amplification products are loaded onto gels, stained with ethidium bromide, and subjected to densitometry analysis. Mean intensities from regions of interest (ROI) that correspond to the bands of interest in the gel are measured.

Gene (or RNA) target quantities obtained by PCR are normalized using the expression level of a housekeeping gene whose expression is constant, such as GAPDH. Expression of the housekeeping gene (or RNA) is analyzed and measured using the same methods as the target.

Probes and primers are designed to hybridize to a C9ORF72 nucleic acid. Methods for designing RT-PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid derived from either DNA strand. For example, antisense oligonucleotides described herein may hybridize to a C9ORF72 antisense transcript or a C9ORF72 sense transcript. Antisense oligonucleotides described herein may hybridize to a C9ORF72 nucleic acid in any stage of RNA processing. Described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72 derived from the sense strand. In certain embodiments, the antisense oligonucleotides described herein selectively hybridize to certain variants of C9ORF72 derived from the sense strand. In certain embodiments, the antisense oligonucleotides described herein selectively hybridize to variants of C9ORF72 derived from the sense strand containing a hexanucleotide repeat expansion. In certain embodiments, the antisense oligonucleotides described herein selectively hybridize to pre-mRNA variants containing a hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72 derived from the sense strand. In certain embodiments, the antisense oligonucleotides described herein inhibit expression of all variants of C9ORF72 derived from the sense strand equally. In certain embodiments, the antisense oligonucleotides described herein preferentially inhibit expression of one or more variants of C9ORF72 derived from the sense strand. In certain embodiments, the antisense oligonucleotides described herein preferentially inhibit expression of variants of C9ORF72 derived from the sense strand containing a hexanucleotide repeat expansion. In certain embodiments, the antisense oligonucleotides described herein selectively inhibit expression of pre-mRNA variants containing the hexanucleotide repeat. In certain embodiments, the antisense oligonucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms C9ORF72 sense foci. In certain embodiments, antisense oligonucleotides described herein are useful for reducing C9ORF72 sense foci. C9ORF72 sense foci may be reduced in terms of percent of cells with foci as well as number of foci per cell.

C9OFF72 Features

Antisense oligonucleotides described herein may hybridize to any C9ORF72 nucleic acid at any state of processing within any element of the C9ORF72 gene. In certain embodiments, antisense oligonucleotides described herein may target the antisense transcript, e.g., SEQ ID NO: 11. In certain embodiments, antisense oligonucleotides described herein may hybridize to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 described below. Antisense oligonucleotides described herein may also target nucleic acids not characterized below and such nucleic acid may be characterized in GENBANK. Moreover, antisense oligonucleotides described herein may also target elements other than exons and such elements as characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
| --- | --- | --- | --- | --- |
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
| --- | --- | --- | --- | --- |
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
| --- | --- | --- | --- | --- |
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
| --- | --- | --- | --- | --- |
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
| --- | --- | --- | --- | --- |
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, administration of an antisense compound targeted to a C9ORF72 antisense transcript results in reduction of C9ORF72 antisense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 antisense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 antisense foci and/or the number of C9ORF72 antisense foci per cell.

In certain embodiments, administration of an antisense compound targeted to a C9ORF72 sense transcript results in reduction of a C9ORF72 sense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 sense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 sense foci and/or the number of C9ORF72 sense foci per cell.

In certain embodiments, pharmaceutical compositions comprising an antisense compound targeted to a C9ORF72 nucleic are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 antisense transcript specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Human Therapeutics

The human C9ORF72 antisense transcript specific antisense compounds described herein are human therapeutics. Various parameters of potency, efficacy, and/or tolerability are being examined. Such parameters include in vitro inhibition of C9ORF72 antisense transcript; in vitro dose response (IC50); in vivo inhibition of C9ORF72 antisense transcript in a transgenic animal containing a human C9ORF72 transgene in relevant tissues (e.g., brain and/or spinal cord); and/or tolerability in mouse, rat, dog, and/or primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of C9ORF72 Antisense Transcript with Oligonucleotides Antisense oligonucleotides (ASOs) targeting the human C9ORF72 antisense transcript were made and tested for inhibition of C9ORF72 antisense transcript in vitro. All of the ASOs in the tables below are 5-10-5 MOE gapmers, 20 nucleosides in length, wherein the central gap segment consists of ten 2'-deoxynucleosides and is flanked by wing segments on the 5' direction and the 3' direction consisting of five nucleosides each. Each nucleoside in the 5' and 3' wing segments has a 2'-MOE modification. The internucleoside linkages throughout each gapmer are phosphorothioate linkages. All cytosine residues throughout each gapmer are 5-methylcytosines. "Start" indicates the 5'-most nucleoside to which the gapmer is targeted in the target transcript sequence. "Stop" indicates the 3'-most nucleoside to which the gapmer is targeted in the target transcript sequence. Each gapmer listed in the tables below is targeted to a putative antisense transcript sequence, designated herein as SEQ ID NO: 11. The sequence of SEQ ID NO: 11 is complementary to nucleotides 1159 to 1929 of SEQ ID NO: 2 (the complement of GENBANK Accession No. NT_008413.18 truncated from nucleotides 27535000 to 27565000) except that SEQ ID NO: 11 has two more six nucleotide repeats than SEQ ID NO: 2. The sequence of the hexanucleotide repeat is GGCCCC in SEQ ID NO: 11 and GGGGCC in SEQ ID NO: 2. Thus, SEQ ID NO: 11 is 12 nucleotides longer than nucleotides 1159 to 1929 of SEQ ID NO: 2, to which it is complementary. Isis No. 129700 is a negative control ASO that does not target the C9ORF72 antisense transcript.

bEND cells were cultured in 24 well plates at 45,000-50,000 cells/well 24 hours before the first of two transfections. The cells were first transfected with 0.2 µg/well of a plasmid expressing the C9ORF72 antisense transcript (SEQ ID NO: 11) and 0.5 µL Lipofectamine 2000 (Life Technologies, Carlsbad, Calif.) in OptiMEM medium. Four to six hours later, the media was replaced. 24 hours after the first transfection (18-20 hours after media replacement), the bEND cells were transfected with 25 nM of an ASO listed in the tables below and 0.5 µL Lipofectamine 2000 in OptiMEM medium or with no ASO. Total RNA was isolated from the cells 24 hours after the second transfection using TRIzol (Life Technologies) according to the manufacturer's directions. Two DNase reactions were performed, one on the column during RNA purification, and one after purification using TURBO DNase (Life Technologies).

Strand specific RT-qPCR was performed on the isolated RNA to generate and amplify C9ORF72 antisense cDNA using one or two of three different primer sets, LTS01222, LTS01221, and C9ATS3'-1. The LTS01222 sequences are: RT primer: CGACTGGAGCACGAGGACACTGAAAAGATGACGCTTGGTGTGTCA (SEQ ID NO: 12), forward PCR primer: CCCACACCTGCTCTTGCTAGA (SEQ ID NO: 13), reverse PCR primer: CGACTGGAGCACGAGGACACTG (SEQ ID NO: 14), and probe: CCCAAAAGAGAAGCAACCGGGCA (SEQ ID NO: 15). The LTS01221 sequences are: RT primer: CGACTGGAGCACGAGGACACTGACGGCTGCCGGGAAGA (SEQ ID NO: 16), forward PCR primer: AGAAATGAGAGGGAAAGTAAAAATGC (SEQ ID NO: 17), reverse PCR primer: CGACTGGAGCACGAGGACACTG (SEQ ID NO: 18), and probe: AGGAGAGCCCCCGCTTCTACCCG (SEQ ID NO: 19). The C9ATS3'-1 sequences are: RT primer: CGACTGGAGCACGAGGACACTGACGCTGAGGGTGAACAAGAA (SEQ ID NO: 20), forward PCR primer: GAGTTCCAGAGCTTGCTACAG (SEQ ID NO: 21), reverse PCR primer: CGACTGGAGCACGAGGACACTG (SEQ ID NO: 22), and probe: CTGCGGTTGTTTCCCTCCTTGTTT (SEQ ID NO: 23). RT-qPCR was also performed on the isolated RNA using Express One-Step Superscript qRT-PCR Kit (Life Technologies, Carlsbad, Calif.) according to manufacturer's instructions to generate and amplify GAPDH cDNA, as a control, using forward PCR primer: GGCAAATTCAACGGCACAGT (SEQ ID NO: 24), reverse PCR primer: GGGTCTCGCTCCTGGAAGAT (SEQ ID NO: 25), and probe: AAGGCCGAGAATGGGAAGCTTGTCATC (SEQ ID NO: 26). The resulting C9ORF72 antisense transcript levels were normalized to GAPDH. These normalized values for C9ORF72 antisense transcript expression in cells treated with an ASO were then compared to the normalized values for C9ORF72 antisense transcript expression in control cells that were transfected with the C9ORF72 antisense plasmid but not an ASO. The results for each primer probe set are shown in the tables below as percent inhibition of C9ORF72 antisense transcript expression relative to the control cells that were not transfected with an ASO. A result of 0% inhibition indicates that the C9ORF72 antisense transcript levels were equal to that of control cells that were not transfected with an ASO. A negative value for % inhibition indicates that the C9ORF72 antisense transcript levels were higher than that of control cells that were not transfected with an ASO. A result of "n/a" indicates that the corresponding primer probe set was not used to analyze the indicated sample. The results show that many ASOs inhibited human C9ORF72 antisense transcript expression. The absolute inhibition results varied across different primer probe sets, but the relative potencies of the ASOs were very similar across different primer probe sets.

TABLE 1

Inhibition of C9ORF72 Antisense Transcript by Antisense Oligonucleotides

| Isis No. | Start | Stop | Sequence | LTS 01222 | LTS 01221 | C9ATS 3'-1 | SEQ ID No. |
|---|---|---|---|---|---|---|---|
| 129700 | n/a | n/a | TAGTGCGGACCTACCCACGA | -28 | 8 | -21 | 41 |
| 661167 | 454<br>460<br>466 | 473<br>479<br>485 | GGGGCCGGGGCCGGGGCCGG | 31 | n/a | n/a | 42 |
| 661168 | 453<br>459<br>465 | 472<br>478<br>484 | GGGCCGGGGCCGGGGCCGGG | 41 | n/a | n/a | 43 |
| 661169 | 452<br>458<br>464 | 471<br>477<br>483 | GGCCGGGGCCGGGGCCGGGG | 51 | n/a | n/a | 44 |
| 661170 | 451<br>457<br>463 | 470<br>476<br>482 | GCCGGGGCCGGGGCCGGGGC | 54 | n/a | n/a | 45 |
| 661171 | 456<br>462 | 475<br>481 | CCGGGGCCGGGGCCGGGGCC | 59 | n/a | n/a | 46 |
| 661172 | 455<br>461 | 474<br>480 | CGGGGCCGGGGCCGGGGCCG | 24 | n/a | n/a | 47 |
| 664570 | 764 | 783 | AGGAAAGAGAGGTGCGTCAA | n/a | 52 | 67 | 48 |
| 664571 | 761 | 780 | AAAGAGAGGTGCGTCAAACA | n/a | 46 | 62 | 49 |
| 664572 | 758 | 777 | GAGAGGTGCGTCAAACAGCG | n/a | 43 | 67 | 50 |
| 664573 | 755 | 774 | AGGTGCGTCAAACAGCGACA | n/a | 35 | 60 | 51 |
| 664574 | 752 | 771 | TGCGTCAAACAGCGACAAGT | n/a | 38 | 63 | 52 |
| 664575 | 749 | 768 | GTCAAACAGCGACAAGTTCC | n/a | 44 | 54 | 53 |
| 664576 | 746 | 765 | AAACAGCGACAAGTTCCGCC | n/a | 19 | 52 | 54 |
| 664577 | 743 | 762 | CAGCGACAAGTTCCGCCCAC | n/a | -5 | -27 | 55 |
| 664578 | 740 | 759 | CGACAAGTTCCGCCCACGTA | n/a | 52 | 51 | 56 |
| 664579 | 737 | 756 | CAAGTTCCGCCCACGTAAAA | n/a | 57 | 38 | 57 |
| 664580 | 734 | 753 | GTTCCGCCCACGTAAAAGAT | n/a | 87 | 92 | 58 |
| 664581 | 731 | 750 | CCGCCCACGTAAAAGATGAC | n/a | 62 | 72 | 59 |
| 664582 | 728 | 747 | CCCACGTAAAAGATGACGCT | n/a | 54 | 58 | 60 |
| 664583 | 725 | 744 | ACGTAAAAGATGACGCTTGG | n/a | 65 | 75 | 61 |
| 664584 | 722 | 741 | TAAAAGATGACGCTTGGTGT | n/a | 61 | 54 | 62 |
| 664585 | 719 | 738 | AAGATGACGCTTGGTGTGTC | n/a | 67 | 77 | 63 |
| 664586 | 716 | 735 | ATGACGCTTGGTGTGTCAGC | n/a | 71 | 72 | 64 |
| 664587 | 713 | 732 | ACGCTTGGTGTGTCAGCCGT | n/a | 45 | 49 | 65 |
| 664588 | 710 | 729 | CTTGGTGTGTCAGCCGTCCC | n/a | 34 | 57 | 66 |
| 664589 | 701 | 720 | TCAGCCGTCCCTGCTGCCCG | n/a | 35 | 40 | 67 |
| 664590 | 698 | 717 | GCCGTCCCTGCTGCCCGGTT | n/a | 17 | 22 | 68 |
| 664591 | 695 | 714 | GTCCCTGCTGCCCGGTTGCT | n/a | 60 | 70 | 69 |
| 664592 | 692 | 711 | CCTGCTGCCCGGTTGCTTCT | n/a | 60 | 83 | 70 |
| 664593 | 689 | 708 | GCTGCCCGGTTGCTTCTCTT | n/a | 41 | 74 | 71 |
| 664594 | 686 | 705 | GCCCGGTTGCTTCTCTTTTG | n/a | 33 | 69 | 72 |

TABLE 1-continued

Inhibition of C9ORF72 Antisense Transcript by Antisense Oligonucleotides

| Isis No. | Start | Stop | Sequence | LTS 01222 | LTS 01221 | C9ATS 3'-1 | SEQ ID No. |
|---|---|---|---|---|---|---|---|
| 664596 | 656 | 675 | CTAGCAAGAGCAGGTGTGGG | n/a | 43 | 47 | 73 |
| 664599 | 647 | 666 | GCAGGTGTGGGTTTAGGAGG | n/a | 40 | 46 | 74 |
| 664600 | 644 | 663 | GGTGTGGGTTTAGGAGGTGT | n/a | 55 | 63 | 75 |
| 664611 | 587 | 606 | GCTCTCACAGTACTCGCTGA | 63 | 49 | n/a | 76 |
| 664613 | 581 | 600 | ACAGTACTCGCTGAGGGTGA | 79 | 48 | n/a | 77 |
| 664623 | 545 | 564 | TAAAGATTAACCAGAAGAAA | 64 | 52 | n/a | 78 |
| 664629 | 509 | 528 | CCGCAGCCTGTAGCAAGCTC | 57 | n/a | n/a | 79 |
| 664635 | 485 | 504 | ACTCAGGAGTCGCGCGCTAG | 64 | n/a | n/a | 80 |

TABLE 2

Inhibition of C9ORF72 Antisense Transcript by Antisense Oligonucleotides

| Isis No. | Start | Stop | Sequence | LTS 01222 | LTS 01221 | C9ATS 3'-1 | SEQ ID No. |
|---|---|---|---|---|---|---|---|
| 129700 | n/a | n/a | TAGTGCGGACCTACCCACGA | 10 | -5 | n/a | 41 |
| 661167 | 454<br>460<br>466 | 473<br>479<br>485 | GGGGCCGGGGCCGGGGCCGG | 69 | 52 | n/a | 42 |
| 661168 | 453<br>459<br>465 | 472<br>478<br>484 | GGGCCGGGGCCGGGGCCGGG | 60 | 36 | n/a | 43 |
| 661169 | 452<br>458<br>464 | 471<br>477<br>483 | GGCCGGGGCCGGGGCCGGGG | 65 | 37 | n/a | 44 |
| 661170 | 451<br>457<br>463 | 470<br>476<br>482 | GCCGGGGCCGGGGCCGGGGC | 66 | 18 | n/a | 45 |
| 661171 | 456<br>462 | 475<br>481 | CCGGGGCCGGGGCCGGGGCC | 77 | 56 | n/a | 46 |
| 661172 | 455<br>461 | 474<br>480 | CGGGGCCGGGGCCGGGGCCG | 65 | 40 | n/a | 47 |

Example 2: Antisense Inhibition of C9ORF72 Antisense Transcript with Oligonucleotides Antisense oligonucleotides (ASOs) described in Example 1 were tested for inhibition of target transcript expression in vitro using a cell line in which a CMV promoter was installed to drive the expression of the endogenous C9ORF72 antisense gene via CRISPR/Cas9 technology.

The targeting portion of a single guide RNA (sgRNA) of the sequence 5'-GACAAGGGTACGTAATCTGTC-3', designated herein as SEQ ID NO: 81, was designed to target a site 1,020 base pairs downstream of the C9ORF72 hexanucleotide repeat. An NGG PAM motif is present at the 3' end of the target site. The targeting portion of the sgRNA was inserted into a dual-expression plasmid to generate the full-length sgRNA of the sequence: 5'-GACAAGGGTACG-TAATCTGTCTAGAGCTAGAAATAGCAAGT-TAAAATAAGGCTAGTCC GTTATCAACTT-GAAAAAGTGGCACCGAGTCGGTGCTTTTTT-3', designated herein as SEQ ID NO: 82 and Cas9 nuclease.

The donor plasmid, containing a 922 base pair 5' homology arm, reverse CMV (CMVr), and 988 base pair 3' homology arm, was generated in pCR4 (Life Technologies) backbone plasmid by Gibson Assembly. The homology arm sequences were designed to center around the CRISPR/Cas9 cleavage site and were constructed using PCR primers: 5'-TAGTCCTGCAGGTTTAAACGAATTCGTGAGT-GAGGAGGCGGCA-3', forward primer, SEQ ID NO: 27, and 5'-AGCAGAGCTCAGATTACGTACCCTTGTTGT-GAACAAC-3', reverse primer, SEQ ID NO: 28, for the 5' arm; and 5'-CAATGTCAACGTCTGGCATTACTTC-TACTTTTG-3', forward primer, SEQ ID NO: 29, and 5'-TAGGGCGAATTGAATTTAGCGGCCGCACTGGCA-GGATCATAGC-3', reverse primer, SEQ ID NO: 30, for the 3' arm. The CMVr sequence was amplified from pCDNA3.1 using PCR primers: 5'-TACGTAATCTGAGCTCTGCT-TATATAGACC-3', forward primer, SEQ ID NO: 31, and 5'-AATGCCAGACGTTGACATTGATTATTGACTAGTT-ATTAATAG-3', reverse primer, SEQ ID NO: 32.

Neuroblast SH-SY5Y cells (Sigma-Aldrich) were cultured in a 1:1 mixture of MEM:F-12 (Life Technologies) supplemented with 10% FBS, 25mM HEPES and Antibiotic-Antimycotic. C9orf72 CRISPR/Cas9 activity was assessed by measuring indel frequency using SURVEYOR mutation detection assay (Integrated DNA Technologies) with forward primer: 5'-GTTAGGCTCTGGGAGAG-TAGTTG-3', SEQ ID NO: 33, and reverse primer: 5'-CCTG-GAGCAGGTAAATGCTGG-3', SEQ ID NO: 34. To generate SH-SY5Y cells expressing C9orf72 antisense transcript, SH-SY5Y cells were transfected with a plasmid expressing C9ORF72 CRISPR sgRNA and Cas9 and with a CMVr donor plasmid. Furthermore, the cells were co-transfected with a plasmid expressing EGFP, then single-cell sorted by FACS into 96-well plates. RT-qPCR was performed to screen for increased C9ORF72 antisense RNA. Positive clones were isolated and validated by PCR using primers inside CMVr and outside the 5' and 3' arms, respectively. Amplicons were further validated by sequencing to confirm on-target insertion of CMVr. Confirmation of single or double allele targeting was obtained by PCR with primers used in the SURVEYOR assay. Sequencing showed that the C9ORF72 antisense transcript contains two full hexanucleotide repeats.

The engineered SH-SY5Y cells were plated at 30,000 cells per well and electroporated at 140V with 10 μM ASO. 24 hours later cells were lysed. Strand specific RT-qPCR was performed on the isolated RNA, as described in Example 1, using the primer probe set LTS01221. The resulting normalized C9ORF72 antisense transcript levels were then compared to the normalized values for C9ORF72 antisense transcript expression in control cells that were transfected with neither the C9ORF72 antisense plasmid nor an ASO. The results are shown in the table below as percent inhibition of C9ORF72 antisense transcript expression relative to the control cells. A result of 0% inhibition indicates that the C9ORF72 antisense transcript levels were equal to that of control cells that were not transfected with an ASO. A negative value for % inhibition indicates that the C9ORF72 antisense transcript levels were higher than that of control cells that were not transfected with an ASO. The results show that many ASOs inhibited human C9ORF72 antisense transcript expression.

TABLE 3

Inhibition of C9ORF72 Antisense Transcript by Antisense Oligonucleotides

| Isis No. | Inhibition (%) | SEQ ID No. |
|---|---|---|
| 129700 | −2 | 41 |
| 664570 | 37 | 48 |
| 664571 | 27 | 49 |
| 664572 | 66 | 50 |
| 664573 | 75 | 51 |
| 664574 | 59 | 52 |
| 664575 | 70 | 53 |
| 664576 | 75 | 54 |
| 664577 | 59 | 55 |
| 664578 | 65 | 56 |
| 664579 | 28 | 57 |
| 664580 | 34 | 58 |
| 664581 | 40 | 59 |
| 664582 | 50 | 60 |
| 664583 | 32 | 61 |

TABLE 3-continued

Inhibition of C9ORF72 Antisense Transcript by Antisense Oligonucleotides

| Isis No. | Inhibition (%) | SEQ ID No. |
|---|---|---|
| 664584 | 48 | 62 |
| 664585 | 56 | 63 |
| 664586 | 66 | 64 |
| 664587 | 77 | 65 |
| 664588 | 64 | 66 |
| 664589 | 61 | 67 |
| 664590 | 59 | 68 |
| 664591 | 60 | 69 |
| 664592 | 62 | 70 |
| 664593 | 69 | 71 |
| 664594 | 67 | 72 |
| 664596 | 41 | 73 |
| 664599 | 26 | 74 |
| 664600 | 50 | 75 |
| 664611 | 68 | 76 |
| 664613 | 58 | 77 |
| 664623 | 3 | 78 |
| 664629 | 76 | 79 |
| 664635 | 60 | 80 |

Example 3: Dose Dependent Inhibition of C9ORF72 Antisense Transcript with Oligonucleotides Isis Numbers 664573, 664575, 664576, 664587, 664593, 664611, and 664629 (see Example 1) were tested for dose dependent inhibition of C9ORF72 antisense transcript expression in vitro. The engineered SH-SY5Y cells described in Example 2 were cultured at 30,000 cells per well and electroporated at 140 V with an oligonucleotide at a concentration listed in the tables below or they received no ASO as a control. 24 hours after electroporation, cells were lysed and total RNA was isolated and analyzed by RT-qPCR using primer probe set LTS01221. The results are shown below for each antisense oligonucleotide concentration, and half maximal inhibitory concentrations were calculated using Prism software (Graphpad).

TABLE 4

Dose Dependent C9ORF72 Antisense Transcript Inhibition

| Isis No. | Concentration (μM) | % Inhibition | IC$_{50}$ (μM) |
|---|---|---|---|
| 664573 | 0.625 | −14 | 3.58 |
|  | 1.25 | 8 |  |
|  | 2.5 | 35 |  |
|  | 5 | 48 |  |
|  | 10 | 66 |  |
|  | 20 | 69 |  |
| 664575 | 0.625 | −14 | 5.36 |
|  | 1.25 | 7 |  |
|  | 2.5 | 17 |  |
|  | 5 | 41 |  |
|  | 10 | 53 |  |
|  | 20 | 72 |  |
| 664576 | 0.625 | −4 | 2.60 |
|  | 1.25 | 4 |  |
|  | 2.5 | 57 |  |
|  | 5 | 51 |  |
|  | 10 | 61 |  |
|  | 20 | 78 |  |
| 664587 | 0.625 | 1 | 2.34 |
|  | 1.25 | 24 |  |
|  | 2.5 | 43 |  |
|  | 5 | 65 |  |
|  | 10 | 61 |  |
|  | 20 | 67 |  |

TABLE 4-continued

Dose Dependent C9ORF72 Antisense Transcript Inhibition

| Isis No. | Concentration (μM) | % Inhibition | IC$_{50}$ (μM) |
|---|---|---|---|
| 664593 | 0.625 | 11 | 2.18 |
| | 1.25 | 27 | |
| | 2.5 | 44 | |
| | 5 | 56 | |
| | 10 | 71 | |
| | 20 | 67 | |
| 664611 | 0.625 | 13 | 2.49 |
| | 1.25 | 25 | |
| | 2.5 | 40 | |
| | 5 | 54 | |
| | 10 | 62 | |
| | 20 | 71 | |

TABLE 5

Dose Dependent C9ORF72 Antisense Transcript Inhibition

| Isis No. | Dose (nM) | % Inhibition | IC$_{50}$ (μM) |
|---|---|---|---|
| 664629 | 0.625 | 13 | 2.63 |
| | 1.25 | 28 | |
| | 2.5 | 36 | |
| | 5 | 49 | |
| | 10 | 64 | |
| | 20 | 68 | |

Example 4: Effect of Antisense Oligonucleotides Targeting C9ORF72 Antisense Transcript on RNA Foci Antisense oligonucleotides targeting the C9ORF72 antisense transcript hexanucleotide repeat, listed in the table below, were tested for their effects on C9ORF72 antisense foci in C9ORF72 ALS/FTD patient fibroblast lines. Each nucleoside of the antisense oligonucleotides in the table below is modified with a 2'-MOE substitution. All of the cytosines are 5-methylcytosines, and all of the internucleoside linkages are phosphorothioate linkages.

TABLE 6

Fully modified antisense oligonucleotides targeting the antisense transcript of C9ORF72

| Isis No. | Sequence | SEQ ID No. |
|---|---|---|
| 663000 | GGGGCCGGGGCCGGGGCCGG | 42 |
| 663001 | GGGCCGGGGCCGGGGCCGGG | 43 |
| 663002 | GGCCGGGGCCGGGGCCGGGG | 44 |
| 663003 | GCCGGGGCCGGGGCCGGGGC | 45 |
| 663004 | CCGGGGCCGGGGCCGGGGCC | 46 |
| 663005 | CGGGGCCGGGGCCGGGGCCG | 47 |

C9ORF72 antisense foci were visualized using fluorescent in situ hybridization with a fluorescently labeled Locked Nucleic Acid (LNA) probe targeting the hexanucleotide repeat containing C9ORF72 antisense transcript (Exiqon, Inc. Woburn Mass.). The sequence of the probe is presented in the table below. The probe was labeled with fluorescent 5' TYE-563. A 5' TYE-563-labeled fluorescent probe targeting CUG repeats is used as a negative control.

TABLE 7

LNA probes to the C9ORF72 antisense transcript containing the hexanucleotide repeat

| Target | Description of probe | Sequence | SEQ ID NO |
|---|---|---|---|
| GGCCCC Repeat of the Antisense Transcript | Fluorescent LNA Probe | TYE563-GGGGCCGGGGCCGGGG | 83 |
| CUG Repeat | Fluorescent LNA Probe | TYE563-CAGCAGCAGCAGCAGCAGC | 84 |

All hybridization steps were performed under RNase-free conditions. Patient fibroblast cells were plated into chamber slides. 24 hours later, they were washed in PBS and transfected with 25 nM of an Isis antisense oligonucleotide in the table below or a negative control ASO that does not target any C9ORF72 RNA using 1 μl/ml Cytofectin transfection reagent (Genlantis, San Diego, Cat #T610001). Cells were incubated for 4 hours at 37° C. and 5% CO$_2$, before the medium was replaced with Dulbecco's modified Eagle medium (DMEM) supplemented with 20% tetracycline-free FBS and 2% penicillin/streptomycin and 1% amphotericin B. 24 hours after transfection, the cells were fixed in 4% PFA, then immediately permeabilized in 0.2% Triton X-100 (Sigma Aldrich #T-8787) in PBS for 10 minutes, washed twice in PBS for 5 minutes, dehydrated with ethanol, and air dried. The slides were heated in 400 μL hybridization buffer (50% deionized formamide, 2×SCC, 50 mM Sodium Phosphate, pH 7, and 10% dextran sulphate) at 66° C. for 20-60 minutes under floating RNase-free coverslips in a chamber humidified with hybridization buffer. Probes were denatured at 80° C. for 75 seconds and returned immediately to ice before diluting with hybridization buffer (40 nM final concentration). The incubating buffer was replaced with the probe-containing mix (400 μL per slide), and slides were hybridized under floating coverslips for 12-16 hours in a sealed, light-protected chamber.

After hybridization, floating coverslips were removed and slides were washed at room temperature in 0.1% Tween-20/2×SCC for 5 minutes before being subjected to three 10-minute stringency washes in 0.1×SCC at 65° C. The slides were then dehydrated through ethanol and air dried.

Primary visualization for quantification and imaging of foci was performed at 100× magnification using a Nikon Eclipse Ti confocal microscope system equipped with a Nikon CFI Apo TIRF 100× Oil objective (NA 1.49). Most foci are intra-nuclear but are also occasionally found in the cytoplasm. Treatment with RNase A, but not DNase I, eliminated the C9ORF72 antisense foci, demonstrating that they are comprised primarily of RNA. The foci in the fibroblasts were counted, and the data is presented in the table below as the number of foci per positive cell and the number of foci per cell overall. (A positive cell is a cell that has at least one focus.) The data in the table below show that treatment with the antisense oligonucleotides targeting the antisense C9ORF72 transcript, listed in the table below, decreased both the number of cells with at least one focus and the number of foci within cells that still had at least one focus.

TABLE 8

Antisense C9ORF72 foci in patient fibroblasts

| Isis No. | Foci per positive cell | Foci per cell |
|---|---|---|
| Negative control ASO | 2.94 | 1.52 |
| 663000 | 1.67 | 0.05 |
| 663001 | 1.20 | 0.12 |
| 663002 | 1.58 | 0.19 |

TABLE 8-continued

Antisense C9ORF72 foci in patient fibroblasts

| Isis No. | Foci per positive cell | Foci per cell |
|---|---|---|
| 663003 | 1.00 | 0.04 |
| 663004 | 2.17 | 0.68 |
| 663005 | 1.86 | 0.36 |

What is claimed is:

1. A compound comprising a modified oligonucleotide consisting of 12-30 linked nucleosides and having a nucleobase sequence comprising consecutive nucleobases of any of the nucleobases sequences of SEQ ID NOs 42-80.

2. The compound of claim 1, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

3. The compound of claim 2, wherein the C9ORF72 antisense transcript has the nucleobase sequence of SEQ ID NO: 11.

4. The compound of claim 3, wherein the modified oligonucleotide is a single-stranded modified oligonucleotide.

5. The compound of claim 4, wherein the modified oligonucleotide comprises at least one modified internucleoside linkage.

6. The compound of claim 5, wherein the at least one modified internucleoside linkage is a phosphorothioate internucleoside linkage.

7. The compound of claim 5, wherein the modified oligonucleotide comprises at least one phosphodiester linkage.

8. The compound of claim 6, wherein each internucleoside linkage is a phosphorothioate internucleoside linkage.

9. The compound of claim 3, wherein at least one nucleoside of the modified oligonucleotide comprises a modified nucleobase.

10. The compound of claim 9, wherein the modified nucleobase is a 5-methylcytosine.

11. The compound of claim 3, wherein at least one nucleoside of the modified oligonucleotide comprises a modified sugar.

12. The compound of claim 11, wherein each nucleoside of the modified oligonucleotide comprises a modified sugar.

13. The compound of claim 11, wherein the modified sugar is a bicyclic sugar.

14. The compound of claim 13, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently selected from H, $C_1$-$C_6$ alkyl, and $C_1$-$C_6$ alkoxy.

15. The compound of claim 14, wherein the chemical bridge is 4'-CH(R)—O-2' and wherein R is methyl.

16. The compound of claim 14, wherein the chemical bridge is 4'-CH(R)—O-2' and wherein R is H.

17. The compound of claim 14, wherein the chemical bridge is 4'-CH(R)—O-2' and wherein R is —CH$_2$—O—CH$_3$.

18. The compound of claim 11, wherein the modified sugar comprises a 2'-O-methoxyethyl group.

19. The compound of claim 4, wherein the modified oligonucleotide is a gapmer.

20. The compound of claim 19, wherein the gapmer is a 5-10-5 MOE gapmer.

21. A composition comprising the compound of claim 3 and at least one of a pharmaceutically acceptable carrier or diluent.

22. A method comprising administering to an animal the compound of claim 3.

23. The method of claim 22, wherein the animal is a human.

24. The method of claim 23, wherein the compound prevents, treats, ameliorates, or slows progression of at least one symptom of a C9ORF72 associated disease.

25. The method of claim 24, wherein the at least one symptom is selected from among impaired motor function, difficulty with respiration, muscle weakness, fasciculation and cramping of muscles, difficulty in projecting the voice, shortness of breath, difficulty in breathing and swallowing, inappropriate social behavior, lack of empathy, distractibility, changes in food preference, agitation, blunted emotions, neglect of personal hygiene, repetitive or compulsive behavior, and decreased energy and motivation.

26. The method of claim 24, wherein the C9ORF72 associated disease is amyotrophic lateral sclerosis (ALS), frontotemporal dementia (FTD), corticobasal degeneration syndrome (CBD), atypical Parkinsonian syndrome, or olivopontocerebellar degeneration (OPCD).

27. The method of claim 26, wherein the amyotrophic lateral sclerosis (ALS) is familial ALS.

28. The method of claim 26, wherein the amyotrophic lateral sclerosis (ALS) is sporadic ALS.

29. The method of claim 23, wherein the administering reduces C9ORF72 antisense transcript associated RAN translation products.

30. The method of claim 29, wherein the C9ORF72 antisense transcript associated RAN translation products are any of poly-(proline-alanine), poly-(proline-arginine), and poly-(proline-glycine).

31. The method of claim 22, wherein the administering reduces C9ORF72 antisense foci.

32. The method of claim 22, wherein the administering is parenteral administration.

33. The method of claim 32, wherein the parenteral administration is any of injection or infusion.

34. The method of claim 33, wherein the parenteral administration is directly into the central nervous system (CNS).

35. The method of claim 34, wherein the parenteral administration is any of intrathecal administration or intracerebroventricular administration.

\* \* \* \* \*

UNITED STATES PATENT AND TRADEMARK OFFICE
CERTIFICATE OF CORRECTION

PATENT NO. : 10,407,678 B2
APPLICATION NO. : 15/565838
DATED : September 10, 2019
INVENTOR(S) : Frank Rigo Page 1 of 1

It is certified that error appears in the above-identified patent and that said Letters Patent is hereby corrected as shown below:

In the Claims

In Claim 1 at Column 119, Line 19, insert --at least 12-- between the words "comprising" and "consecutive."

Signed and Sealed this
Twenty-second Day of December, 2020

Andrei Iancu
*Director of the United States Patent and Trademark Office*